(12) United States Patent
Chen et al.

(10) Patent No.: US 7,553,377 B1
(45) Date of Patent: Jun. 30, 2009

(54) APPARATUS AND METHOD FOR ELECTROSTATIC COATING OF AN ABLUMINAL STENT SURFACE

(75) Inventors: Yung-Ming Chen, Cupertino, CA (US); Fuh-Wei Tang, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 517 days.

(21) Appl. No.: 10/833,902

(22) Filed: Apr. 27, 2004

(51) Int. Cl.
*B05C 13/02* (2006.01)
*B05B 5/00* (2006.01)
*B05B 5/16* (2006.01)

(52) U.S. Cl. .................. 118/500; 118/624; 118/630

(58) Field of Classification Search .............. 118/500, 118/503, 307, DIG. 11, 624, 628, 620, 621, 118/630, 502; 427/2.1, 2.24, 2.25, 2.28, 427/458; 623/1.46, 1.47, 1.48
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 2,647,017 A | 7/1953 | Coulliette | |
| 2,701,559 A | 2/1955 | Cooper | |
| 3,288,728 A | 11/1966 | Gorham | |
| 3,687,135 A | 8/1972 | Stroganov et al. | |
| 3,773,737 A | 11/1973 | Goodman et al. | |
| 3,839,743 A | 10/1974 | Schwarcz | |
| 3,849,514 A | 11/1974 | Gray, Jr. et al. | |
| 3,900,632 A | 8/1975 | Robinson | |
| 4,075,045 A | 2/1978 | Rideout | |
| 4,104,410 A | 8/1978 | Malecki | |
| 4,110,497 A | 8/1978 | Hoel | |
| 4,132,357 A | 1/1979 | Blackinton | |
| 4,164,524 A | 8/1979 | Ward et al. | |
| 4,226,243 A | 10/1980 | Shalaby et al. | |
| 4,321,711 A | 3/1982 | Mano | |
| 4,323,071 A | 4/1982 | Simpson et al. | |
| 4,323,525 A * | 4/1982 | Bornat ........................ 264/441 |
| 4,329,383 A | 5/1982 | Joh | |
| 4,338,942 A | 7/1982 | Fogarty | |
| 4,343,931 A | 8/1982 | Barrows | |
| 4,346,028 A | 8/1982 | Griffith | |
| 4,439,185 A | 3/1984 | Lundquist | |
| 4,489,670 A | 12/1984 | Mosser et al. | |
| 4,516,972 A | 5/1985 | Samson et al. | |
| 4,529,792 A | 7/1985 | Barrows | |
| 4,538,622 A | 9/1985 | Samson et al. | |
| 4,554,929 A | 11/1985 | Samson et al. | |

(Continued)

FOREIGN PATENT DOCUMENTS

CA          2 008 312          7/1990

(Continued)

OTHER PUBLICATIONS

U.S. Appl. No. 10/255,913, filed Sep. 26, 2002, Tang et al.

(Continued)

*Primary Examiner*—Yewebdar T Tadesse
(74) *Attorney, Agent, or Firm*—Squire, Sanders & Dempsey, L.L.P.

(57) ABSTRACT

A stent mandrel fixture for supporting a stent during the electrostatic application of a coating substance is provided.

18 Claims, 5 Drawing Sheets

U.S. PATENT DOCUMENTS

| | | |
|---|---|---|
| 4,573,470 A | 3/1986 | Fogarty |
| 4,596,574 A | 6/1986 | Urist |
| 4,599,085 A | 7/1986 | Riess et al. |
| 4,608,984 A | 9/1986 | Powell |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Brooks et al. |
| 4,629,563 A | 12/1986 | Wrasidlo |
| 4,633,873 A | 1/1987 | Dumican et al. |
| 4,638,805 A | 1/1987 | Simpson |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Palmaz |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,768,507 A | 9/1988 | Fischell et al. |
| 4,774,039 A | 9/1988 | Wrasidlo |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,828,561 A | 5/1989 | Woodroof |
| 4,850,999 A | 7/1989 | Planck |
| 4,865,870 A | 9/1989 | Hu et al. |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |
| 4,882,168 A | 11/1989 | Casey et al. |
| 4,886,062 A | 12/1989 | Wiktor |
| 4,902,289 A | 2/1990 | Yannas |
| 4,906,423 A | 3/1990 | Frisch |
| 4,926,788 A * | 5/1990 | Metcalf ............... 118/500 |
| 4,931,287 A | 6/1990 | Bae et al. |
| 4,932,353 A | 6/1990 | Kawata et al. |
| 4,941,870 A | 7/1990 | Okada et al. |
| 4,943,346 A | 7/1990 | Mattelin |
| 4,950,227 A | 8/1990 | Savin et al. |
| 4,955,899 A | 9/1990 | Della Corna et al. |
| 4,967,606 A | 11/1990 | Wells et al. |
| 4,977,901 A | 12/1990 | Ofstead |
| 4,988,356 A | 1/1991 | Crittenden et al. |
| 4,994,033 A | 2/1991 | Shockey et al. |
| 4,994,298 A | 2/1991 | Yasuda |
| 4,994,560 A | 2/1991 | Kruper, Jr. et al. |
| 5,015,505 A | 5/1991 | Cetnar |
| 5,019,090 A | 5/1991 | Pinchuk |
| 5,019,096 A | 5/1991 | Fox, Jr. et al. |
| 5,028,597 A | 7/1991 | Kodama et al. |
| 5,037,392 A | 8/1991 | Hillstead |
| 5,037,427 A | 8/1991 | Harada et al. |
| 5,040,548 A | 8/1991 | Yock |
| 5,047,050 A | 9/1991 | Arpesani |
| 5,049,132 A | 9/1991 | Shaffer et al. |
| 5,053,048 A | 10/1991 | Pinchuk |
| 5,059,166 A | 10/1991 | Fischell |
| 5,059,169 A | 10/1991 | Zilber |
| 5,059,211 A | 10/1991 | Stack et al. |
| 5,062,829 A | 11/1991 | Pryor et al. |
| 5,064,435 A | 11/1991 | Porter |
| 5,078,720 A | 1/1992 | Burton et al. |
| 5,081,394 A | 1/1992 | Morishita et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,087,394 A | 2/1992 | Keith |
| 5,100,429 A | 3/1992 | Sinofsky et al. |
| 5,100,992 A | 3/1992 | Cohn et al. |
| 5,102,402 A | 4/1992 | Dror et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,318 A | 5/1992 | Hillstead |
| 5,116,365 A | 5/1992 | Hillstead |
| 5,123,917 A | 6/1992 | Lee |
| 5,127,362 A | 7/1992 | Iwatsu et al. |
| 5,133,742 A | 7/1992 | Pinchuk |
| 5,134,192 A | 7/1992 | Feijen et al. |
| 5,147,370 A | 9/1992 | McNamara et al. |
| 5,156,623 A | 10/1992 | Hakamatsuka et al. |
| 5,156,911 A | 10/1992 | Stewart |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,171,445 A | 12/1992 | Zepf |
| 5,176,638 A | 1/1993 | Don Michael |
| 5,188,734 A | 2/1993 | Zepf |
| 5,192,311 A | 3/1993 | King et al. |
| 5,197,977 A | 3/1993 | Hoffman, Jr. et al. |
| 5,205,822 A | 4/1993 | Johnson et al. |
| 5,213,561 A | 5/1993 | Weinstein et al. |
| 5,213,576 A | 5/1993 | Abiuso et al. |
| 5,219,980 A | 6/1993 | Swidler |
| 5,222,971 A | 6/1993 | Willard et al. |
| 5,225,750 A | 7/1993 | Higuchi et al. |
| 5,226,889 A | 7/1993 | Sheiban |
| 5,226,913 A | 7/1993 | Pinchuk |
| 5,229,045 A | 7/1993 | Soldani |
| 5,229,172 A | 7/1993 | Cahalan et al. |
| 5,232,444 A | 8/1993 | Just et al. |
| 5,234,456 A | 8/1993 | Silvestrini |
| 5,234,457 A | 8/1993 | Andersen |
| 5,236,447 A | 8/1993 | Kubo et al. |
| 5,242,399 A | 9/1993 | Lau et al. |
| 5,254,089 A | 10/1993 | Wang |
| 5,254,091 A | 10/1993 | Aliahmad et al. |
| 5,258,020 A | 11/1993 | Froix |
| 5,258,419 A | 11/1993 | Rolando et al. |
| 5,269,802 A | 12/1993 | Garber |
| 5,272,012 A | 12/1993 | Opolski |
| 5,278,200 A | 1/1994 | Coury et al. |
| 5,279,594 A | 1/1994 | Jackson |
| 5,282,823 A | 2/1994 | Schwartz et al. |
| 5,282,860 A | 2/1994 | Matsuno et al. |
| 5,286,254 A | 2/1994 | Shapland et al. |
| 5,289,831 A | 3/1994 | Bosley |
| 5,290,271 A | 3/1994 | Jernberg |
| 5,292,516 A | 3/1994 | Viegas et al. |
| 5,298,260 A | 3/1994 | Viegas et al. |
| 5,300,295 A | 4/1994 | Viegas et al. |
| 5,304,200 A | 4/1994 | Spaulding |
| 5,306,250 A | 4/1994 | March et al. |
| 5,306,286 A | 4/1994 | Stack et al. |
| 5,306,294 A | 4/1994 | Winston et al. |
| 5,306,501 A | 4/1994 | Viegas et al. |
| 5,306,786 A | 4/1994 | Moens et al. |
| 5,308,641 A | 5/1994 | Cahalan et al. |
| 5,314,472 A | 5/1994 | Fontaine |
| 5,318,531 A | 6/1994 | Leone |

| Patent No. | Date | Inventor |
|---|---|---|
| 5,328,471 A | 7/1994 | Slepian |
| 5,330,500 A | 7/1994 | Song |
| 5,330,768 A | 7/1994 | Park et al. |
| 5,336,518 A | 8/1994 | Narayanan et al. |
| 5,342,283 A | 8/1994 | Good |
| 5,342,348 A | 8/1994 | Kaplan |
| 5,342,395 A | 8/1994 | Jarrett et al. |
| 5,342,621 A | 8/1994 | Eury |
| 5,344,426 A | 9/1994 | Lau et al. |
| 5,344,455 A | 9/1994 | Keogh et al. |
| 5,350,800 A | 9/1994 | Verhoeven et al. |
| 5,356,433 A | 10/1994 | Rowland et al. |
| 5,360,401 A | 11/1994 | Turnland et al. |
| 5,360,443 A | 11/1994 | Barone et al. |
| 5,364,354 A | 11/1994 | Walker et al. |
| 5,366,504 A | 11/1994 | Andersen et al. |
| 5,368,560 A | 11/1994 | Rambo et al. |
| 5,370,684 A | 12/1994 | Vallana et al. |
| 5,380,299 A | 1/1995 | Fearnot et al. |
| 5,383,925 A | 1/1995 | Schmitt |
| 5,383,927 A | 1/1995 | DeGoicoechea et al. |
| 5,385,580 A | 1/1995 | Schmitt |
| 5,387,450 A | 2/1995 | Stewart |
| 5,389,106 A | 2/1995 | Tower |
| 5,399,666 A | 3/1995 | Ford |
| 5,405,472 A | 4/1995 | Leone |
| 5,409,495 A | 4/1995 | Osborn |
| 5,411,466 A | 5/1995 | Hess |
| 5,411,477 A | 5/1995 | Saab |
| 5,412,035 A | 5/1995 | Schmitt et al. |
| 5,415,938 A | 5/1995 | Cahalan et al. |
| 5,417,981 A | 5/1995 | Endo et al. |
| 5,423,849 A | 6/1995 | Engelson et al. |
| 5,423,885 A | 6/1995 | Williams |
| 5,429,618 A | 7/1995 | Keogh |
| 5,441,515 A | 8/1995 | Khosravi et al. |
| 5,443,458 A | 8/1995 | Eury et al. |
| 5,443,496 A | 8/1995 | Schwartz et al. |
| 5,443,500 A | 8/1995 | Sigwart |
| 5,445,646 A | 8/1995 | Euteneuer et al. |
| 5,447,724 A | 9/1995 | Helmus et al. |
| 5,451,233 A | 9/1995 | Yock |
| 5,455,040 A | 10/1995 | Marchant |
| 5,456,661 A | 10/1995 | Narciso, Jr. |
| 5,456,713 A | 10/1995 | Chuter |
| 5,458,615 A | 10/1995 | Klemm et al. |
| 5,460,610 A | 10/1995 | Don Michael |
| 5,462,990 A | 10/1995 | Hubbell et al. |
| 5,464,450 A | 11/1995 | Buscemi et al. |
| 5,464,650 A | 11/1995 | Berg et al. |
| 5,470,313 A | 11/1995 | Crocker et al. |
| 5,470,603 A | 11/1995 | Staniforth et al. .......... 427/2.14 |
| 5,476,476 A | 12/1995 | Hillstead |
| 5,476,509 A | 12/1995 | Keogh et al. |
| 5,485,496 A | 1/1996 | Lee et al. |
| 5,496,346 A | 3/1996 | Horzewski et al. |
| 5,500,013 A | 3/1996 | Buscemi et al. |
| 5,501,227 A | 3/1996 | Yock |
| 5,502,158 A | 3/1996 | Sinclair et al. |
| 5,507,768 A | 4/1996 | Lau et al. |
| 5,511,726 A | 4/1996 | Greenspan et al. |
| 5,514,154 A | 5/1996 | Lau et al. |
| 5,514,379 A | 5/1996 | Weissleder et al. |
| 5,516,560 A | 5/1996 | Harayama et al. |
| 5,516,881 A | 5/1996 | Lee et al. |
| 5,527,337 A | 6/1996 | Stack et al. |
| 5,537,729 A | 7/1996 | Kolobow |
| 5,538,493 A | 7/1996 | Gerken et al. |
| 5,545,209 A | 8/1996 | Roberts et al. |
| 5,545,408 A | 8/1996 | Trigg et al. |
| 5,551,954 A | 9/1996 | Buscemi et al. |
| 5,554,120 A | 9/1996 | Chen et al. |
| 5,554,182 A | 9/1996 | Dinh et al. |
| 5,556,413 A | 9/1996 | Lam |
| 5,558,642 A | 9/1996 | Schweich, Jr. et al. |
| 5,562,728 A | 10/1996 | Lazarus et al. |
| 5,569,463 A | 10/1996 | Helmus et al. |
| 5,571,135 A | 11/1996 | Fraser et al. |
| 5,571,166 A | 11/1996 | Dinh et al. |
| 5,571,567 A | 11/1996 | Shah |
| 5,578,046 A | 11/1996 | Liu et al. |
| 5,578,073 A | 11/1996 | Haimovich et al. |
| 5,584,877 A | 12/1996 | Miyake et al. |
| 5,588,962 A | 12/1996 | Nicholas et al. |
| 5,591,199 A | 1/1997 | Porter et al. |
| 5,591,224 A | 1/1997 | Schwartz et al. |
| 5,591,227 A | 1/1997 | Dinh et al. |
| 5,591,607 A | 1/1997 | Gryaznov et al. |
| 5,593,403 A | 1/1997 | Buscemi |
| 5,593,434 A | 1/1997 | Williams |
| 5,595,722 A | 1/1997 | Grainger et al. |
| 5,599,301 A | 2/1997 | Jacobs et al. |
| 5,599,307 A | 2/1997 | Bacher et al. |
| 5,599,352 A | 2/1997 | Dinh et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,609,629 A | 3/1997 | Fearnot et al. |
| 5,610,241 A | 3/1997 | Lee et al. |
| 5,611,775 A | 3/1997 | Machold et al. |
| 5,616,338 A | 4/1997 | Fox, Jr. et al. |
| 5,618,298 A | 4/1997 | Simon |
| 5,618,299 A | 4/1997 | Khosravi et al. |
| 5,620,420 A | 4/1997 | Kriesel |
| 5,624,411 A | 4/1997 | Tuch |
| 5,628,730 A | 5/1997 | Shapland et al. |
| 5,628,755 A | 5/1997 | Heller et al. |
| 5,628,781 A | 5/1997 | Williams et al. |
| 5,628,785 A | 5/1997 | Schwartz et al. |
| 5,628,786 A | 5/1997 | Banas et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,644,020 A | 7/1997 | Timmermann et al. |
| 5,645,559 A | 7/1997 | Hachtman et al. |
| 5,649,951 A | 7/1997 | Davidson |
| 5,649,977 A | 7/1997 | Campbell |
| 5,653,691 A | 8/1997 | Rupp et al. |
| 5,656,080 A | 8/1997 | Staniforth et al. ............. 118/20 |
| 5,656,082 A | 8/1997 | Takatsuki et al. |
| 5,658,995 A | 8/1997 | Kohn et al. |
| 5,667,523 A | 9/1997 | Bynon et al. |
| 5,667,767 A | 9/1997 | Greff et al. |
| 5,667,796 A | 9/1997 | Otten |
| 5,670,558 A | 9/1997 | Onishi et al. |
| 5,674,242 A | 10/1997 | Phan et al. |
| 5,679,400 A | 10/1997 | Tuch |
| 5,693,085 A | 12/1997 | Buirge et al. |
| 5,693,376 A | 12/1997 | Fetherston et al. |
| 5,695,498 A | 12/1997 | Tower |
| 5,695,810 A | 12/1997 | Dubin et al. |
| 5,697,967 A | 12/1997 | Dinh et al. |
| 5,700,286 A | 12/1997 | Tartaglia et al. |
| 5,702,754 A | 12/1997 | Zhong |
| 5,702,818 A | 12/1997 | Cahalan et al. |
| 5,707,385 A | 1/1998 | Williams |
| 5,711,763 A | 1/1998 | Nonami et al. |
| 5,711,812 A | 1/1998 | Chapek et al. |
| 5,711,958 A | 1/1998 | Cohn et al. |
| 5,713,949 A | 2/1998 | Jayaraman |
| 5,716,981 A | 2/1998 | Hunter et al. |
| 5,718,726 A | 2/1998 | Amon et al. |
| 5,720,726 A | 2/1998 | Marcadis et al. |

| | | | | | |
|---|---|---|---|---|---|
| 5,721,131 A | 2/1998 | Rudolph et al. | 5,853,408 A | 12/1998 | Muni |
| 4,733,665 A | 3/1998 | Palmaz | 5,854,207 A | 12/1998 | Lee et al. |
| 5,722,984 A | 3/1998 | Fischell et al. | 5,854,376 A | 12/1998 | Higashi |
| 5,723,219 A | 3/1998 | Kolluri et al. | 5,855,598 A | 1/1999 | Pinchuk |
| 5,725,549 A | 3/1998 | Lam | 5,855,612 A | 1/1999 | Ohthuki et al. |
| 5,726,297 A | 3/1998 | Gryaznov et al. | 5,855,618 A | 1/1999 | Patnaik et al. |
| 5,728,068 A | 3/1998 | Leone et al. | 5,857,998 A | 1/1999 | Barry |
| 5,728,751 A | 3/1998 | Patnaik | 5,858,556 A | 1/1999 | Eckert et al. |
| 5,730,698 A | 3/1998 | Fischell et al. | 5,858,746 A | 1/1999 | Hubbell et al. |
| 5,733,326 A | 3/1998 | Tomonto et al. | 5,858,990 A | 1/1999 | Walsh |
| 5,733,327 A | 3/1998 | Igaki et al. | 5,860,954 A | 1/1999 | Ropiak |
| 5,733,330 A | 3/1998 | Cox | 5,865,814 A | 2/1999 | Tuch |
| 5,733,564 A | 3/1998 | Lehtinen | 5,866,113 A | 2/1999 | Hendriks et al. |
| 5,733,925 A | 3/1998 | Kunz et al. | 5,868,781 A | 2/1999 | Killion |
| 5,735,897 A | 4/1998 | Buirge | 5,869,127 A | 2/1999 | Zhong |
| 5,741,554 A | 4/1998 | Tisone | 5,871,436 A | 2/1999 | Eury |
| 5,741,881 A | 4/1998 | Patnaik | 5,871,437 A | 2/1999 | Alt |
| 5,746,745 A | 5/1998 | Abele et al. | 5,873,904 A | 2/1999 | Ragheb et al. |
| 5,746,998 A | 5/1998 | Torchilin et al. | 5,874,101 A | 2/1999 | Zhong et al. |
| 5,756,457 A | 5/1998 | Wang et al. | 5,874,109 A | 2/1999 | Ducheyne et al. |
| 5,756,476 A | 5/1998 | Epstein et al. | 5,874,165 A | 2/1999 | Drumheller |
| 5,759,205 A | 6/1998 | Valentini | 5,874,355 A | 2/1999 | Huang et al. |
| 5,759,474 A | 6/1998 | Rupp et al. | 5,876,426 A | 3/1999 | Kume et al. |
| 5,765,682 A | 6/1998 | Bley et al. | 5,876,433 A | 3/1999 | Lunn |
| 5,766,204 A | 6/1998 | Porter et al. | 5,876,743 A | 3/1999 | Ibsen et al. |
| 5,766,239 A | 6/1998 | Cox | 5,877,224 A | 3/1999 | Brocchini et al. |
| 5,766,710 A | 6/1998 | Turnlund et al. | 5,877,263 A | 3/1999 | Patnaik et al. |
| 5,769,883 A | 6/1998 | Buscemi et al. | 5,879,713 A | 3/1999 | Roth et al. |
| 5,769,884 A | 6/1998 | Solovay | 5,883,011 A | 3/1999 | Lin et al. |
| 5,770,609 A | 6/1998 | Grainger et al. | 5,888,533 A | 3/1999 | Dunn |
| 5,772,864 A | 6/1998 | Møller et al. | 5,891,192 A | 4/1999 | Murayama et al. |
| 5,776,184 A | 7/1998 | Tuch | 5,893,840 A | 4/1999 | Hull et al. |
| 5,780,807 A | 7/1998 | Saunders | 5,893,852 A | 4/1999 | Morales |
| 5,782,742 A | 7/1998 | Crocker et al. | 5,895,407 A | 4/1999 | Jayaraman |
| 5,783,657 A | 7/1998 | Pavlin et al. | 5,897,911 A | 4/1999 | Loeffler |
| 5,788,626 A | 8/1998 | Thompson | 5,897,955 A | 4/1999 | Drumheller |
| 5,788,979 A | 8/1998 | Alt et al. | 5,898,178 A | 4/1999 | Bunker |
| 5,800,392 A | 9/1998 | Racchini | 5,902,631 A | 5/1999 | Wang et al. |
| 5,800,516 A | 9/1998 | Fine et al. | 5,902,875 A | 5/1999 | Roby et al. |
| 5,804,318 A | 9/1998 | Pinchuk et al. | 5,905,168 A | 5/1999 | Dos Santos et al. |
| 5,807,244 A | 9/1998 | Barot | 5,906,759 A | 5/1999 | Richter |
| 5,810,871 A | 9/1998 | Tuckey et al. | 5,910,564 A | 6/1999 | Gruning et al. |
| 5,810,873 A | 9/1998 | Morales | 5,914,182 A | 6/1999 | Drumheller |
| 5,811,151 A | 9/1998 | Hendriks et al. | 5,914,387 A | 6/1999 | Roby et al. |
| 5,811,447 A | 9/1998 | Kunz et al. | 5,916,234 A | 6/1999 | Lam |
| 5,820,917 A | 10/1998 | Tuch | 5,916,870 A | 6/1999 | Lee et al. |
| 5,823,996 A | 10/1998 | Sparks | 5,919,893 A | 7/1999 | Roby et al. |
| 5,824,048 A | 10/1998 | Tuch | 5,921,416 A | 7/1999 | Uchara |
| 5,824,049 A | 10/1998 | Ragheb et al. ............ 623/1 | 5,922,005 A | 7/1999 | Richter et al. |
| 5,824,056 A | 10/1998 | Rosenberg | 5,922,393 A | 7/1999 | Jayaraman |
| 5,826,586 A | 10/1998 | Mishra et al. | 5,925,552 A | 7/1999 | Keogh et al. |
| 5,830,178 A | 11/1998 | Jones et al. | 5,925,720 A | 7/1999 | Kataoka et al. |
| 5,830,179 A | 11/1998 | Mikus et al. | 5,928,916 A | 7/1999 | Keogh |
| 5,830,217 A | 11/1998 | Ryan | 5,932,299 A | 8/1999 | Katoot |
| 5,830,461 A | 11/1998 | Billiar | 5,935,135 A | 8/1999 | Bramfitt et al. |
| 5,830,879 A | 11/1998 | Isner | 5,942,209 A | 8/1999 | Leavitt et al. |
| 5,833,644 A | 11/1998 | Zadno-Azizi et al. | 5,947,993 A | 9/1999 | Morales |
| 5,833,651 A | 11/1998 | Donovan et al. | 5,948,018 A | 9/1999 | Dereume et al. |
| 5,833,659 A | 11/1998 | Kranys | 5,948,428 A | 9/1999 | Lee et al. |
| 5,834,582 A | 11/1998 | Sinclair et al. | 5,951,881 A | 9/1999 | Rogers et al. |
| 5,836,962 A | 11/1998 | Gianotti | 5,954,744 A | 9/1999 | Phan et al. |
| 5,836,965 A | 11/1998 | Jendersee et al. | 5,955,509 A | 9/1999 | Webber et al. |
| 5,837,008 A | 11/1998 | Berg et al. | 5,957,975 A | 9/1999 | Lafont et al. |
| 5,837,313 A | 11/1998 | Ding et al. | 5,958,385 A | 9/1999 | Tondeur et al. |
| 5,837,835 A | 11/1998 | Gryaznov et al. | 5,962,138 A | 10/1999 | Kolluri et al. |
| 5,840,009 A | 11/1998 | Fischell et al. | 5,965,720 A | 10/1999 | Gryaznov et al. |
| 5,840,083 A | 11/1998 | Braach-Maksvytis | 5,968,091 A | 10/1999 | Pinchuk et al. |
| 5,843,033 A | 12/1998 | Ropiak | 5,968,092 A | 10/1999 | Buscemi et al. |
| 5,843,119 A | 12/1998 | Schulewitz | 5,969,422 A | 10/1999 | Ting et al. |
| 5,843,172 A | 12/1998 | Yan | 5,971,954 A | 10/1999 | Conway et al. |
| 5,846,247 A | 12/1998 | Unsworth et al. | 5,972,027 A | 10/1999 | Johnson |
| 5,849,859 A | 12/1998 | Acemoglu | 5,972,029 A | 10/1999 | Fuisz |
| 5,851,508 A | 12/1998 | Greff et al. | 5,972,505 A | 10/1999 | Phillips et al. |

| | | | | | |
|---|---|---|---|---|---|
| 5,976,155 A | 11/1999 | Foreman et al. | 6,120,788 A | 9/2000 | Barrows |
| 5,976,182 A | 11/1999 | Cox | 6,120,847 A | 9/2000 | Yang et al. |
| 5,980,564 A | 11/1999 | Stinson | 6,120,904 A | 9/2000 | Hostettler et al. |
| 5,980,928 A | 11/1999 | Terry | 6,121,027 A | 9/2000 | Clapper et al. |
| 5,980,972 A | 11/1999 | Ding | 6,123,712 A | 9/2000 | Di Caprio et al. |
| 5,981,568 A | 11/1999 | Kunz et al. | 6,125,523 A | 10/2000 | Brown et al. |
| 5,984,449 A | 11/1999 | Tajika et al. | 6,126,686 A | 10/2000 | Badylak et al. |
| 5,986,169 A | 11/1999 | Gjunter | 6,127,173 A | 10/2000 | Eckstein et al. |
| 5,997,468 A | 12/1999 | Wolff et al. | 6,129,761 A | 10/2000 | Hubbell |
| 5,997,517 A | 12/1999 | Whitbourne | 6,129,928 A | 10/2000 | Sarangapani et al. |
| 6,010,445 A | 1/2000 | Armini et al. | 6,132,809 A | 10/2000 | Hynes et al. |
| 6,010,530 A | 1/2000 | Goicoechea | 6,136,333 A | 10/2000 | Cohn et al. |
| 6,010,573 A | 1/2000 | Bowlin | 6,140,127 A | 10/2000 | Sprague |
| 6,011,125 A | 1/2000 | Lohmeijer et al. | 6,140,431 A | 10/2000 | Kinker et al. |
| 6,013,099 A | 1/2000 | Dinh et al. | 6,143,354 A | 11/2000 | Koulik et al. |
| 6,015,541 A | 1/2000 | Greff et al. | 6,143,370 A | 11/2000 | Panagiotou et al. |
| 6,019,789 A | 2/2000 | Dinh et al. | 6,149,574 A | 11/2000 | Trauthen et al. |
| 6,024,918 A | 2/2000 | Hendriks et al. | 6,150,630 A | 11/2000 | Perry et al. |
| 6,027,510 A | 2/2000 | Alt | 6,153,252 A | 11/2000 | Hossainy et al. |
| 6,027,526 A | 2/2000 | Limon et al. | 6,156,373 A | 12/2000 | Zhong et al. |
| 6,030,371 A | 2/2000 | Pursley | 6,159,227 A | 12/2000 | Di Caprio et al. |
| 6,033,582 A | 3/2000 | Lee et al. | 6,159,229 A | 12/2000 | Jendersee et al. |
| 6,033,719 A | 3/2000 | Keogh | 6,159,951 A | 12/2000 | Karpeisky et al. |
| 6,034,204 A | 3/2000 | Mohr et al. | 6,159,978 A | 12/2000 | Myers et al. |
| 6,042,606 A | 3/2000 | Frantzen | 6,160,084 A | 12/2000 | Langer et al. |
| 6,042,875 A | 3/2000 | Ding et al. | 6,165,212 A | 12/2000 | Dereume et al. |
| 6,045,899 A | 4/2000 | Wang et al. | 6,166,130 A | 12/2000 | Rhee et al. |
| 6,048,964 A | 4/2000 | Lee et al. | 6,168,617 B1 | 1/2001 | Blaeser et al. |
| 6,051,021 A | 4/2000 | Frid | 6,168,619 B1 | 1/2001 | Dinh et al. |
| 6,051,576 A | 4/2000 | Ashton et al. | 6,169,170 B1 | 1/2001 | Gryaznov et al. |
| 6,051,648 A | 4/2000 | Rhee et al. | 6,171,609 B1 | 1/2001 | Kunz |
| 6,054,553 A | 4/2000 | Groth et al. | 6,172,167 B1 | 1/2001 | Stapert et al. |
| 6,056,906 A | 5/2000 | Werneth et al. | 6,174,316 B1 | 1/2001 | Tuckey et al. |
| 6,056,993 A | 5/2000 | Leidner et al. | 6,174,330 B1 | 1/2001 | Stinson |
| 6,059,752 A | 5/2000 | Segal | 6,177,523 B1 | 1/2001 | Reich et al. |
| 6,059,810 A | 5/2000 | Brown et al. | 6,180,632 B1 | 1/2001 | Myers et al. |
| 6,060,451 A | 5/2000 | DiMaio et al. | 6,183,505 B1 | 2/2001 | Mohn, Jr. et al. |
| 6,060,518 A | 5/2000 | Kabanov et al. | 6,187,045 B1 | 2/2001 | Fehring et al. |
| 6,063,092 A | 5/2000 | Shin | 6,193,727 B1 | 2/2001 | Foreman et al. |
| 6,066,156 A | 5/2000 | Yan | 6,203,551 B1 | 3/2001 | Wu |
| 6,071,266 A | 6/2000 | Kelley | 6,209,621 B1 | 4/2001 | Treacy |
| 6,071,305 A | 6/2000 | Brown et al. | 6,210,715 B1 | 4/2001 | Starling et al. |
| 6,074,659 A | 6/2000 | Kunz et al. | 6,211,249 B1 | 4/2001 | Cohn et al. |
| 6,080,099 A | 6/2000 | Slater et al. | 6,214,115 B1 | 4/2001 | Taylor et al. |
| 6,080,177 A | 6/2000 | Igaki et al. | 6,214,407 B1 | 4/2001 | Laube et al. |
| 6,080,190 A | 6/2000 | Schwartz | 6,214,901 B1 | 4/2001 | Chudzik et al. |
| 6,080,488 A | 6/2000 | Hostettler et al. | 6,217,586 B1 | 4/2001 | Mackenzie |
| 6,083,258 A | 7/2000 | Yadav | 6,217,721 B1 | 4/2001 | Xu et al. |
| 6,086,610 A | 7/2000 | Duerig et al. | 6,224,626 B1 | 5/2001 | Steinke |
| 6,090,330 A | 7/2000 | Gawa et al. | 6,224,675 B1 | 5/2001 | Prentice et al. |
| 6,093,199 A | 7/2000 | Brown et al. | 6,224,894 B1 | 5/2001 | Jamiolkowski et al. |
| 6,093,463 A | 7/2000 | Thakrar | 6,227,110 B1 | 5/2001 | Morales |
| 6,096,070 A | 8/2000 | Ragheb et al. ............ 623/1 | 6,228,845 B1 | 5/2001 | Donovan et al. |
| 6,096,525 A | 8/2000 | Patnaik | 6,231,590 B1 | 5/2001 | Slaikeu et al. |
| 6,099,455 A | 8/2000 | Columbo et al. | 6,231,600 B1 | 5/2001 | Zhong |
| 6,099,559 A | 8/2000 | Nolting | 6,240,616 B1 | 6/2001 | Yan |
| 6,099,561 A | 8/2000 | Alt | 6,242,041 B1 | 6/2001 | Katoot et al. |
| 6,099,562 A | 8/2000 | Ding et al. | 6,245,076 B1 | 6/2001 | Yan |
| 6,103,230 A | 8/2000 | Billiar et al. | 6,245,099 B1 | 6/2001 | Edwin et al. |
| 6,106,454 A | 8/2000 | Berg et al. | 6,245,103 B1 | 6/2001 | Stinson |
| 6,106,530 A | 8/2000 | Harada | 6,245,753 B1 | 6/2001 | Byun et al. |
| 6,106,889 A | 8/2000 | Beavers et al. | 6,245,760 B1 | 6/2001 | He et al. |
| 6,107,416 A | 8/2000 | Patnaik et al. | 6,248,129 B1 | 6/2001 | Froix |
| 6,110,180 A | 8/2000 | Foreman et al. | 6,248,344 B1 | 6/2001 | Ylanen et al. |
| 6,110,188 A | 8/2000 | Narciso, Jr. | 6,251,135 B1 | 6/2001 | Stinson et al. |
| 6,110,483 A | 8/2000 | Whitbourne et al. | 6,251,136 B1 | 6/2001 | Guruwaiya et al. |
| 6,113,629 A | 9/2000 | Ken | 6,251,142 B1 | 6/2001 | Bernacca et al. |
| 6,117,479 A | 9/2000 | Hogan et al. ............ 427/2.14 | 6,253,443 B1 | 7/2001 | Johnson |
| 6,117,979 A | 9/2000 | Hendriks et al. | 6,254,632 B1 | 7/2001 | Wu et al. |
| 6,120,477 A | 9/2000 | Campbell et al. | 6,258,099 B1 | 7/2001 | Mareiro et al. |
| 6,120,491 A | 9/2000 | Kohn et al. | 6,258,121 B1 | 7/2001 | Yang et al. |
| 6,120,535 A | 9/2000 | McDonald et al. | 6,258,371 B1 | 7/2001 | Koulik et al. |
| 6,120,536 A | 9/2000 | Ding et al. | 6,262,034 B1 | 7/2001 | Mathiowitz et al. |

| Patent | Kind | Date | Inventor |
|---|---|---|---|
| 6,270,788 | B1 | 8/2001 | Koulik et al. |
| 6,273,850 | B1 | 8/2001 | Gambale |
| 6,273,913 | B1 | 8/2001 | Wright et al. |
| 6,277,110 | B1 | 8/2001 | Morales |
| 6,277,449 | B1 | 8/2001 | Kolluri et al. |
| 6,279,368 | B1 | 8/2001 | Escano et al. |
| 6,281,262 | B1 | 8/2001 | Shikinami |
| 6,283,947 | B1 | 9/2001 | Mirzaee |
| 6,283,949 | B1 | 9/2001 | Roorda |
| 6,284,305 | B1 | 9/2001 | Ding et al. |
| 6,284,333 | B1 | 9/2001 | Wang et al. |
| 6,287,332 | B1 | 9/2001 | Bolz et al. |
| 6,287,628 | B1 | 9/2001 | Hossainy et al. |
| 6,290,721 | B1 | 9/2001 | Heath |
| 6,293,966 | B1 | 9/2001 | Frantzen |
| 6,294,836 | B1 | 9/2001 | Paranjpe et al. |
| 6,296,603 | B1 | 10/2001 | Turnlund et al. |
| 6,299,604 | B1 | 10/2001 | Ragheb et al. |
| 6,303,901 | B1 | 10/2001 | Perry et al. |
| 6,306,176 | B1 | 10/2001 | Whitbourne |
| 6,312,459 | B1 | 11/2001 | Huang et al. |
| 6,319,520 | B1 | 11/2001 | Wuthrich et al. |
| 6,322,588 | B1 | 11/2001 | Ogle et al. |
| 6,322,847 | B1 | 11/2001 | Zhong et al. |
| 6,327,772 | B1 | 12/2001 | Zadno-Azizi et al. |
| 6,331,313 | B1 | 12/2001 | Wong et al. |
| 6,335,029 | B1 | 1/2002 | Kamath et al. |
| 6,344,035 | B1 | 2/2002 | Chudzik et al. |
| 6,346,110 | B2 | 2/2002 | Wu |
| 6,358,556 | B1 | 3/2002 | Ding et al. |
| 6,362,099 | B1 | 3/2002 | Gandikota et al. |
| 6,364,903 | B2 | 4/2002 | Tseng et al. |
| 6,375,458 | B1 | 4/2002 | Moorleghem et al. |
| 6,375,826 | B1 | 4/2002 | Wang et al. |
| 6,379,379 | B1 | 4/2002 | Wang |
| 6,379,381 | B1 | 4/2002 | Hossainy et al. |
| 6,387,118 | B1 | 5/2002 | Hanson |
| 6,387,121 | B1 | 5/2002 | Alt |
| 6,387,379 | B1 | 5/2002 | Goldberg et al. |
| 6,388,043 | B1 | 5/2002 | Langer et al. |
| 6,395,325 | B1 | 5/2002 | Hedge et al. |
| 6,395,326 | B1 | 5/2002 | Castro et al. |
| 6,406,738 | B1 | 6/2002 | Hogan et al. ............... 427/2.14 |
| 6,409,761 | B1 | 6/2002 | Jang |
| 6,413,272 | B1 | 7/2002 | Igaki |
| 6,419,692 | B1 | 7/2002 | Yang et al. |
| 6,420,189 | B1 | 7/2002 | Lopatin |
| 6,423,092 | B2 | 7/2002 | Datta et al. |
| 6,436,816 | B1 | 8/2002 | Lee et al. |
| 6,444,567 | B1 | 9/2002 | Besser et al. |
| 6,447,835 | B1 | 9/2002 | Wang et al. |
| 6,451,373 | B1 | 9/2002 | Hossainy et al. |
| 6,454,738 | B1 | 9/2002 | Tran et al. |
| 6,455,424 | B1 | 9/2002 | McTeer et al. |
| 6,461,632 | B1 | 10/2002 | Gogolewski |
| 6,462,284 | B1 | 10/2002 | Hashimoto |
| 6,464,720 | B2 | 10/2002 | Boatman et al. |
| 6,468,906 | B1 | 10/2002 | Chan et al. |
| 6,479,565 | B1 | 11/2002 | Stanley |
| 6,481,262 | B2 | 11/2002 | Ching et al. |
| 6,482,834 | B2 | 11/2002 | Spada et al. |
| 6,485,512 | B1 | 11/2002 | Cheng |
| 6,488,701 | B1 | 12/2002 | Nolting et al. |
| 6,488,773 | B1 | 12/2002 | Ehrhardt et al. |
| 6,491,666 | B1 | 12/2002 | Santini, Jr. et al. |
| 6,492,615 | B1 | 12/2002 | Flanagan |
| 6,494,862 | B1 | 12/2002 | Ray et al. |
| 6,494,908 | B1 | 12/2002 | Huxel et al. |
| 6,495,156 | B2 | 12/2002 | Wenz et al. |
| 6,495,200 | B1 | 12/2002 | Chan et al. |
| 6,503,538 | B1 | 1/2003 | Chu et al. |
| 6,503,556 | B2 | 1/2003 | Harish et al. |
| 6,503,954 | B1 | 1/2003 | Bhat et al. |
| 6,504,307 | B1 | 1/2003 | Malik et al. |
| 6,506,437 | B1 | 1/2003 | Harish et al. |
| 6,510,722 | B1 | 1/2003 | Ching et al. |
| 6,511,748 | B1 | 1/2003 | Barrows |
| 6,517,888 | B1 | 2/2003 | Weber |
| 6,517,889 | B1 | 2/2003 | Jayaraman |
| 6,521,284 | B1 | 2/2003 | Parsons et al. |
| 6,524,232 | B1 | 2/2003 | Tang et al. |
| 6,524,347 | B1 | 2/2003 | Myers et al. |
| 6,527,801 | B1 | 3/2003 | Dutta |
| 6,527,863 | B1 | 3/2003 | Pacetti et al. |
| 6,528,526 | B1 | 3/2003 | Myers et al. |
| 6,530,950 | B1 | 3/2003 | Alvarado et al. |
| 6,530,951 | B1 | 3/2003 | Bates et al. |
| 6,537,589 | B1 | 3/2003 | Chae et al. |
| 6,539,607 | B1 | 4/2003 | Fehring et al. |
| 6,540,776 | B2 | 4/2003 | Sanders Millare et al. |
| 6,540,777 | B2 | 4/2003 | Stenzel |
| 6,544,223 | B1 | 4/2003 | Kokish |
| 6,544,543 | B1 | 4/2003 | Mandrusov et al. |
| 6,544,582 | B1 | 4/2003 | Yoe |
| 6,554,758 | B2 | 4/2003 | Turnlund et al. |
| 6,554,854 | B1 | 4/2003 | Flanagan |
| 6,555,059 | B1 | 4/2003 | Myrick et al. |
| 6,555,157 | B1 | 4/2003 | Hossainy |
| 6,558,733 | B1 | 5/2003 | Hossainy et al. |
| 6,562,136 | B1 | 5/2003 | Chappa et al. |
| 6,565,599 | B1 | 5/2003 | Hong et al. |
| 6,565,659 | B1 | 5/2003 | Pacetti et al. |
| 6,569,191 | B1 | 5/2003 | Hogan |
| 6,569,193 | B1 | 5/2003 | Cox et al. |
| 6,572,644 | B1 | 6/2003 | Moein |
| 6,572,672 | B2 | 6/2003 | Yadav et al. |
| 6,574,851 | B1 | 6/2003 | Mirizzi |
| 6,582,417 | B1 | 6/2003 | Ledesma et al. |
| 6,585,755 | B2 | 7/2003 | Jackson et al. |
| 6,585,765 | B1 | 7/2003 | Hossainy et al. |
| 6,585,926 | B1 | 7/2003 | Mirzaee |
| 6,592,614 | B2 | 7/2003 | Lenker et al. |
| 6,592,617 | B2 | 7/2003 | Thompson |
| 6,596,296 | B1 | 7/2003 | Nelson et al. |
| 6,605,114 | B1 | 8/2003 | Yan et al. |
| 6,605,154 | B1 | 8/2003 | Villareal |
| 6,605,874 | B2 | 8/2003 | Leu et al. |
| 6,610,087 | B1 | 8/2003 | Zarbatany et al. |
| 6,613,072 | B2 | 9/2003 | Lau et al. |
| 6,616,765 | B1 | 9/2003 | Hossanoy et al. |
| 6,623,448 | B2 | 9/2003 | Slater |
| 6,625,486 | B2 | 9/2003 | Lundkvist et al. |
| 6,626,939 | B1 | 9/2003 | Burnside et al. |
| 6,635,269 | B1 | 10/2003 | Jennissen |
| 6,635,964 | B2 | 10/2003 | Maex et al. |
| 6,645,135 | B1 | 11/2003 | Bhat |
| 6,645,195 | B1 | 11/2003 | Bhat et al. |
| 6,645,243 | B2 | 11/2003 | Vallana et al. |
| 6,645,547 | B1 | 11/2003 | Shekalim et al. |
| 6,656,162 | B2 | 12/2003 | Santini, Jr. et al. |
| 6,656,216 | B1 | 12/2003 | Hossainy et al. |
| 6,656,506 | B1 | 12/2003 | Wu et al. |
| 6,660,034 | B1 | 12/2003 | Mandrusov et al. |
| 6,663,662 | B2 | 12/2003 | Pacetti et al. |
| 6,663,880 | B1 | 12/2003 | Roorda et al. |
| 6,664,187 | B1 | 12/2003 | Ngo et al. |
| 6,664,335 | B2 | 12/2003 | Krishnan |
| 6,666,214 | B2 | 12/2003 | Canham |
| 6,666,880 | B1 | 12/2003 | Chiu et al. |
| 6,667,049 | B2 | 12/2003 | Janas et al. |
| 6,669,723 | B2 | 12/2003 | Killion et al. |
| 6,669,980 | B2 | 12/2003 | Hansen ............... 427/2.24 |
| 6,673,154 | B1 | 1/2004 | Pacetti et al. |
| 6,673,385 | B1 | 1/2004 | Ding et al. |
| 6,676,697 | B1 | 1/2004 | Richter |
| 6,676,700 | B1 | 1/2004 | Jacobs et al. |

| | | |
|---|---|---|
| 6,679,980 B1 | 1/2004 | Andreacchi |
| 6,689,099 B2 | 2/2004 | Mirzaee |
| 6,689,375 B1 | 2/2004 | Wahlig et al. |
| 6,695,920 B1 | 2/2004 | Pacetti et al. |
| 6,699,281 B2 | 3/2004 | Vallana et al. |
| 6,703,307 B2 | 3/2004 | Lopatin et al. |
| 6,706,013 B1 | 3/2004 | Bhat et al. |
| 6,706,273 B1 | 3/2004 | Roessler |
| 6,709,379 B1 | 3/2004 | Brandau et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,752,826 B2 | 6/2004 | Holloway et al. |
| 6,753,007 B2 | 6/2004 | Haggard et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,774,278 B1 | 8/2004 | Ragheb et al. |
| 6,776,792 B1 | 8/2004 | Yan et al. |
| 6,783,793 B1 | 8/2004 | Hossainy et al. |
| 6,818,063 B1 | 11/2004 | Kerrigan |
| 6,846,323 B2 | 1/2005 | Yip et al. |
| 6,860,946 B2 | 3/2005 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,731 B2 | 5/2005 | Li et al. |
| 2001/0007083 A1 | 7/2001 | Roorda |
| 2001/0014717 A1 | 8/2001 | Hossainy et al. |
| 2001/0016753 A1 | 8/2001 | Caprio et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0044652 A1 | 11/2001 | Moore |
| 2001/0051608 A1 | 12/2001 | Mathiowitz et al. |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0062148 A1 | 5/2002 | Hart |
| 2002/0065553 A1 | 5/2002 | Weber |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0116050 A1 | 8/2002 | Kocur |
| 2002/0120326 A1 | 8/2002 | Michal |
| 2002/0138133 A1 | 9/2002 | Lenz et al. |
| 2002/0142039 A1 | 10/2002 | Claude |
| 2002/0155212 A1 | 10/2002 | Hossainy |
| 2002/0161114 A1 | 10/2002 | Gunatillake et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0187632 A1 | 12/2002 | Marsh |
| 2002/0188037 A1 | 12/2002 | Chudzik et al. |
| 2002/0188277 A1 | 12/2002 | Roorda et al. |
| 2003/0003221 A1 | 1/2003 | Zhong et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0033001 A1 | 2/2003 | Igaki |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0054090 A1 | 3/2003 | Hansen ........................ 427/2.1 |
| 2003/0055482 A1 | 3/2003 | Schwager et al. |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0088307 A1 | 5/2003 | Shulze et al. |
| 2003/0093107 A1 | 5/2003 | Parsonage et al. |
| 2003/0097088 A1 | 5/2003 | Pacetti |
| 2003/0097173 A1 | 5/2003 | Dutta |
| 2003/0099712 A1 | 5/2003 | Jayaraman |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0113439 A1 | 6/2003 | Pacetti et al. |
| 2003/0113445 A1 | 6/2003 | Martin ........................ 427/180 |
| 2003/0138487 A1 | 7/2003 | Hogan et al. ................ 424/474 |
| 2003/0143315 A1* | 7/2003 | Pui et al. ..................... 427/2.1 |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0171053 A1 | 9/2003 | Sanders |
| 2003/0185964 A1 | 10/2003 | Weber et al. ............... 427/2.25 |
| 2003/0187495 A1 | 10/2003 | Cully et al. |
| 2003/0190406 A1 | 10/2003 | Hossainy et al. |
| 2003/0203617 A1 | 10/2003 | Lane et al. |
| 2003/0207020 A1 | 11/2003 | Villareal |
| 2003/0208259 A1 | 11/2003 | Penhasi |
| 2003/0209835 A1 | 11/2003 | Chun et al. |
| 2003/0211230 A1 | 11/2003 | Pacetti et al. |
| 2003/0226833 A1 | 12/2003 | Shapovalov et al. |
| 2003/0236565 A1 | 12/2003 | DiMatteo et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0093077 A1 | 5/2004 | White et al. |
| 2004/0096504 A1 | 5/2004 | Michal |

| | | | |
|---|---|---|---|
| 2004/0098095 A1 | 5/2004 | Burnside et al. | |
| 2004/0098117 A1 | 5/2004 | Hossainy et al. | |
| 2004/0111149 A1 | 6/2004 | Stinson | |
| 2004/0127970 A1 | 7/2004 | Saunders | |
| 2004/0142015 A1 | 7/2004 | Hossainy et al. | |
| 2004/0143317 A1 | 7/2004 | Stinson et al. | |
| 2004/0167610 A1 | 8/2004 | Fleming, III | |
| 2004/0213893 A1 | 10/2004 | Boulais | |
| 2005/0038497 A1 | 2/2005 | Neuendorf et al. | |
| 2005/0043786 A1 | 2/2005 | Chu et al. | |
| 2005/0049694 A1 | 3/2005 | Neary | |
| 2005/0054774 A1 | 3/2005 | Kangas | |
| 2005/0055044 A1 | 3/2005 | Kangas | |
| 2005/0060020 A1 | 3/2005 | Jenson | |
| 2005/0064088 A1 | 3/2005 | Fredrickson | |
| 2005/0065501 A1 | 3/2005 | Wallace | |
| 2005/0065545 A1 | 3/2005 | Wallace | |
| 2005/0065593 A1 | 3/2005 | Chu et al. | |
| 2005/0074406 A1 | 4/2005 | Couvillon, Jr. et al. | |
| 2005/0074545 A1 | 4/2005 | Thomas | |
| 2005/0079274 A1 | 4/2005 | Palasis et al. | |

FOREIGN PATENT DOCUMENTS

| | | |
|---|---|---|
| CA | 2 007 648 | 4/1991 |
| CA | 1 322 628 | 10/1993 |
| CA | 1 336 319 | 7/1995 |
| CA | 1 338 303 | 5/1996 |
| DE | 042 24 401 | 1/1994 |
| DE | 044 07 079 | 9/1994 |
| DE | 197 31 021 | 1/1999 |
| DE | 199 16 086 | 10/1999 |
| DE | 198 56 983 | 12/1999 |
| EP | 0 108 171 | 5/1984 |
| EP | 0 144 534 | 6/1985 |
| EP | 0 301 856 | 2/1989 |
| EP | 0 380 668 | 4/1989 |
| EP | 0 351 314 | 1/1990 |
| EP | 0 364 787 | 4/1990 |
| EP | 0 396 429 | 11/1990 |
| EP | 0 397 500 | 11/1990 |
| EP | 0 464 755 | 1/1992 |
| EP | 0 493 788 | 7/1992 |
| EP | 0526606 B1 | 9/1992 |
| EP | 0 514 406 | 11/1992 |
| EP | 0 517 075 | 12/1992 |
| EP | 0 540 290 | 5/1993 |
| EP | 0 553 960 | 8/1993 |
| EP | 0 554 082 | 8/1993 |
| EP | 0 565 251 | 10/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 627 226 | 12/1994 |
| EP | 0 649 637 | 4/1995 |
| EP | 0 665 023 | 8/1995 |
| EP | 0 701 802 | 3/1996 |
| EP | 0 701 803 | 3/1996 |
| EP | 0 709 068 | 5/1996 |
| EP | 0 716 836 | 6/1996 |
| EP | 0 732 087 | 9/1996 |
| EP | 0 832 618 | 9/1996 |
| EP | 0 756 853 | 2/1997 |
| EP | 0 809 999 | 12/1997 |
| EP | 0 832 655 | 4/1998 |
| EP | 0 834 293 | 4/1998 |
| EP | 0 850 604 | 7/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 972 498 | 1/2000 |
| EP | 0 974 315 | 1/2000 |
| EP | 0 982 041 | 3/2000 |
| EP | 1 023 879 | 8/2000 |
| EP | 1 034 752 | 9/2000 |
| EP | 1075838 A2 | 2/2001 |
| EP | 1 103 234 | 5/2001 |
| EP | 1 192 957 | 4/2002 |
| EP | 1 273 314 | 1/2003 |
| EP | 0869847 B1 | 3/2003 |
| EP | 0941072 B1 | 1/2004 |
| FR | 2 753 907 | 4/1998 |
| GB | 2 247 696 | 3/1992 |
| GB | 2 316 086 | 1/2000 |
| GB | 216086 B1 | 1/2000 |
| GB | 2316342 B | 1/2000 |
| GB | 2333975 B | 1/2000 |
| GB | 2336551 B | 1/2000 |
| GB | 2356586 A | 5/2001 |
| GB | 2356587 A | 5/2001 |
| GB | 2333474 B | 6/2001 |
| GB | 2334685 B | 6/2001 |
| GB | 2356585 B | 7/2001 |
| GB | 2374302 A | 8/2001 |
| GB | 2370243 A | 6/2002 |
| GB | 2384199 A | 7/2003 |
| JP | SHO49-48336 | 12/1974 |
| JP | SHO54-18310 | 7/1979 |
| JP | SHO60-28504 | 7/1985 |
| JP | 21199867 | 5/1994 |
| JP | HEI8-33718 | 2/1996 |
| JP | HEI10-151190 | 6/1998 |
| JP | 2919971 | 7/1999 |
| JP | 2001-190687 | 7/2001 |
| SU | 1016314 | 5/1973 |
| SU | 0872531 | 10/1981 |
| SU | 0876663 | 10/1981 |
| SU | 0905228 | 2/1982 |
| SU | 0790725 | 2/1983 |
| SU | 0811750 | 9/1983 |
| SU | 1293518 | 2/1987 |
| SU | 1477423 | 5/1989 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/11176 | 8/1991 |
| WO | WO 91/12846 | 9/1991 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/09760 | 5/1994 |
| WO | WO 94/21196 | 9/1994 |
| WO | WO 95/10989 | 4/1995 |
| WO | WO 95/11817 | 5/1995 |
| WO | WO 95/24929 | 9/1995 |
| WO | WO 95/29647 | 11/1995 |
| WO | WO 95/33422 | 12/1995 |
| WO | WO 96/28115 | 9/1996 |
| WO | WO 96/35516 | 11/1996 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/04415 | 2/1998 |
| WO | WO 98/07390 | 2/1998 |
| WO | WO 98/08463 | 3/1998 |
| WO | WO 98/17331 | 4/1998 |
| WO | WO 98/20863 | 5/1998 |
| WO | WO 98/23228 | 6/1998 |
| WO | WO 98/32398 | 7/1998 |

| | | |
|---|---|---|
| WO | WO 98/36784 | 8/1998 |
| WO | WO 99/01118 | 1/1999 |
| WO | WO 99/03515 | 1/1999 |
| WO | WO 99/16386 | 4/1999 |
| WO | WO 99/38546 | 8/1999 |
| WO | WO 99/42147 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17459 | 3/2001 |
| WO | WO 01/17577 | 3/2001 |
| WO | WO 01/43727 | 6/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/47731 | 6/2002 |
| WO | WO 02/49771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |
| WO | WO 2004/017947 | 3/2004 |
| WO | WO 2004/017976 | 3/2004 |
| WO | WO 2004/023985 | 3/2004 |
| WO | WO 2004/024339 | 3/2004 |

OTHER PUBLICATIONS

U.S. Appl. No. 10/304,669, filed Nov. 25, 2002, Madriaga et al.
U.S. Appl. No. 10/317,435, filed Dec. 11, 2002, Hossainy et al.
U.S. Appl. No. 10/322,255, filed Dec. 17, 2002, Chen et al.
U.S. Appl. No. 10/409,410, filed Apr. 7, 2003, Pacetti.
U.S. Appl. No. 10/439,415, filed May 15, 2003, Perng.
U.S. Appl. No. 10/602,487, filed Jun. 23, 2003, Castro et al.
U.S. Appl. No. 10/630,250, filed Jul. 30, 2003, Pacetti et al.
U.S. Appl. No. 10/676,545, filed Sep. 30, 2003, Fox et al.
U.S. Appl. No. 10/680,905, filed Oct. 7, 2003, Pacetti et al.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/747,996, filed Dec. 29, 2003, Chen et al.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/824,754, filed Apr. 15, 2004, Perng.
Angioplasty.org., *Balloons and Stents*, http://www.ptca.org/devices04.html, printed Oct. 15, 2004, 2 pages.
Anonymous, *Capillary Action*, http://www.ndt-ed.org/EducationResources/CommunityCollege/PenetrantTest/Introduction/Keywords/pt1.htm, printed Aug. 12, 2005, 1 page.
Anonymous, *Capillary Force Lithography (CFL)*, Nano Processing and Organic Devices Lab, 2 pages (no date).
Anonymous, *Capillary Rise of Liquid in Different Varies Under Variable Residual Acceleration*, http://www.zarm.uni-bremen.de/2forschung/grenzph/isoterm/cap_rise/kapst_en.htm, ZARM—University of Bremen, printed Jun. 25, 2003, 2 pages.
Anonymous, *Cardiologists Draw—Up The Dream Stent*, Clinica 710, pp. 15 (Jun. 17, 1996), http://www.dialogweb.com/cgi/document?reg=1061848202959, printed Aug. 25, 2003, 2 pages.
Anonymous, *Coating Techniques, Air Knife Coating*, http://www.ferron-magnetic.co.uk/coatings/airknife.htm, printed Jul. 1, 2003, 1 page.
Anonymous, *Coating Techniques, Gap Coating (Knife Over Roll, etc.)*, http://www.ferron-magnetic.co.uk/coatings/knife.htm, printed Jul. 1, 2003, 1 page.
Anonymous, Coating *Techniques, Gravure Coating*, http://www.ferron-magnetic.co.uk/coatings/gravure.htm, printed Jul. 1, 2003, 2 pages.
Anonymous, *Coating Techniques, Reverse Roll Coating*, http://www.ferron-magnetic.co.uk/coatings/revroll.htm, printed Jul. 1, 2003, 22 pages.
Anonymous, *Heparin-coated stents cut complications By 30%*, Clinica 732, pp. 17 (Nov. 18, 1996), http://www.dialogweb.com/cgi/document?reg=1061847871753, printed Aug. 25, 2003, 2 pages.
Anonymous, *Liquid Gravity Motor*, http://w__ww.drspark86.com/idea001.html, printed Jun. 24, 2003, 2 pages (no date).
Anonymous, *Porosimetry—Why characterize the porosity?* 42 pages (no date.).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting Continues to Dominate Cardiology*, http://www.dialogweb.com/cgi/document?reg=1061848017752, Clinica vol. 720, pp. 22 (Sep. 2, 1996), printed Aug. 25, 2003, 2 pages.
Anonymous, *Surface Energy (Surface Wetting Capability)*, http://www.ndt-ed.org/EducationResources/CommunityCollege/PenetrantTest/PTMaterials/surfaceenergy/.htm, printed Apr. 6, 2004, 3 pages (no date).
Anonymous, *The 14th International Young Physicists Tournament, The winning report*, Research Center for Quantum Information, Slovak Academy of Sciences, 5 pages (no date).
Anonymous, *The Wicking Well System*, http://www.decorative.com/wicking.html, printed Jun. 24, 2003, 1 page.
Anonymous, *Typical Parylene Properties*, 3 pages (no date).
Anonymous, *Viscosity*, Commonwealth of Australia, 7 pages (no date).
Ansari, *End-to-End Tubal Anastomosis Using an Absorbable Stent*, Fertility and Sterility, vol. 32, No. 2, pp. 197-201 (Aug. 1979).
Ansari, *Tubal Reanastomosis Using Absorbable Stent*, International Journal of Fertility, vol. 23, No. 4, pp. 242-243 (1978).
Aoyagi et al., *Preparation of cross-linked aliphatic polyester and application to thermo-responsive material*, Journal of Controlled Release 32, pp. 87-96 (1994).
Barath et al., *Low Dose of Antitumor Agents Prevents Smooth Muscle Cell Proliferation After Endothelial Injury*, JACC vol. 3, No. 2, pp. 252A (Feb. 1989).
Barbucci et al., *Coating of commercially available materials with a new heparinizable Material*, Journal of Biomedical Materials Research, vol. 25, pp. 1259-1274 (1991).
Beach et al., *Xylylene Polymers*, Encyclopedia of Polymer Science and Engineering, vol. 17, 2nd Edition pp. 990-1025 (1989).
Boston Scientific, Express[2]™ *Coronary Stent System*, http://www.bostonscientific.com/med_specialty/deviceDetail.jsp?task=tskBasicDevice.jsp&sectionId=4&relId=2,74,75,76&deviceId=11001&uniqueId=MPDB1180&clickType=endeca, printed Aug. 8, 2005, 1 page.
Bull, *Parylene Coating for Medical Applications*, Medical Product Manufacturing News, 2 pages (Mar. 1993).

Casper et al., *Fiber-Reinforced Absorbable Composite for Orthopedic Surgery*, Polymeric Materials Science and Engineering, vol. 53, pp. 497-501(1985).

Charlson et al., *Temperature Selective Deposition of Parylene-C*, IEEE Transactions of Biomedical Engineering, vol. 39, No. 2, pp. 202-206 (Feb. 1992).

Chen et al., *The Kinetics of Wicking of Liquid Droplets into Yarns*, submitted to the Textile Research Journal, pp. 1-30 (Apr. 2001).

Chung et al., *Inner core segment design for drug delivery control of thermo-responsive polymeric micelles*, Journal of Controlled Release, vol. 65, pp. 93-103 (2000).

Crowe et al., *Absorption and Intestinal Metabolism of SDZ-RAD and Rapamycin in Rats*, Drug Metabolism and Disposition, vol. 27, No. 5, pp. 627-632 (1999).

De Scheerder et al., *Biocompatibility of polymer-coated oversized metallic stents implanted in normal porcine coronary arteries*, Atherosclerosis, vol. 114, pp. 105-114 (1995).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9, No. 6, pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis, vol. 34, pp. 272-278 (1995).

Devanathan et al., *Polymeric Conformal Coatings for Implantable Electronic Devices*, IEEE Transactions on Biomedical Engineering, vol. BME-27, No. 11, pp. 671-675 (1980).

Dichek et al., *Seeding of Intravascular Stents with Genetically Engineered Endothelial Cells*, Circulation, vol. 80, No. 5, pp. 1347-1353 (Nov. 1989).

Dreyer et al., *Critical Velocities in Open Capillary Flows*, pp. 604-609 (no date).

Duerig et al., *A comparison of balloon-and self-expanding stents*, Min. Invas. Ther. & Allied Technol., vol. 11, No. 4, pp. 173-178 (2002).

Dutkiewicz, *Some Advances in Nonwoven Structures for Absorbency, Comfort and Aesthetics*, AUTEX Research Journal, vol. 2, No. 3, pp. 153-165 (Sep. 2002).

EFD, *780S Series Spray Valves VALVEMATE™ 7040 Controller Operating Manual*, 24 pages (2002).

Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).

Elbert et al., *Conjugate Addition Reactions Combined with Free-Radical Cross-Linking for the Design of Materials for Tissue Engineering*, Biomacromolecules, vol. 2, pp. 430-441 (2001).

Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascualr Prosthetic Materials*, J. Biomed. Mater. Res. vol. 10, pp. 113-122 (1976).

Eskin et al., *Tissue Cultured Cells: Potential Blood Compatible Linings for Cardiovascular Prostheses*, Polymer Science and Technology, vol. 14, pp. 143-161 (no date).

Fischell et al., *Low-Dose, β-Particle Emission for 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx Velocity™ Stent*, 5 pages, Biocompatibles Ltd. (2001).

Gengenbach et al., *Evolution of the Surface Composition and Topography of Perflurinated Polymers Following Ammonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol. 56, No. 3, pp. 353-360 (2002).

Gölander et al., *RF-Plasma-Modified Polystyrene Surfaces for Studying Complement Activation*, J. Biomater. Sci. Plymer Edn., vol. 4, No. 1 pp. 25-30 (1992).

Guidant, *ACS RX Multi-Link™ Coronary Stent System*, 6 pages (no date).

Guidant, *Guidant Multi-Link Vision OTW Coronary Stent System*, 2 pages (no date).

Hahn et al., *Biocompatibility of Glow-Discharge-Polmerized Films and Vacuum-Deposited Parylene*, Journal of Applied Polymer Science: Appled Polymer Symposium 38, 55-64 (1984).

Hahn et al., *Glow Discharge Polymers as Coatings for Implanted Devices*, John M. Dalton Research Center, University of Missouri-Columbia and the Graduate Center for Materials Research, pp. 109-113 (1981).

He et al., *Assessment of Tissue Blood Flow Following Small Artery Welding with an Intraluminal Dissolvable Stent*, Microsurgery, vol. 19, No. 3, pp. 148-152 (1999).

Hehrlein et al., *Low-Dose Radioactive Endovascular Stents Prevent Smooth Muscle Cell Proliferation and Neointimal Hyperplasia in Rabbits*, Circulation, vol. 92, No. 6, pp. 1570-1575 (Sep. 15, 1995).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol., vol. 3, pp. 197-199 (1998).

Hollahan et al., *Attachment of Amino Groups to Polymer Surfaces by Radiofrequency Plasmas*, Journal of Applied Polymer Science, vol. 13, pp. 807-816 (1969).

Huang et al., *Biodegradable Polymers Derived from Aminoacids*, Macromol. Symp. 144, 7-32 (1999).

Impulse Jetting, *About Us*, http://www.impulsejetting.com/about.html, printed Dec. 18, 2000, 1 page.

Impulse Jetting, *Our Technology*, http://www.impulsejetting.com/tech1.html, printed Dec. 18, 2000, 1 page.

Inagaki et al., *Hyrophilic Surface Modification of Polyethylene by No-Plasma Treatment*, Adhesion Sci. Technol., vol. 4, No. 2, pp. 99-107 (1990).

Inoue et al., *An AB block copolymer of oligo(methyl methacrylate) and poly(acrylic acid) for micellar delivery of hydrophobic drugs*, Journal of Controlled Release, vol. 51, pp. 221-229 (1998).

Itabashi et al., *Electroless Deposited CoWB for Copper Diffusion Barrier Metal*, International Interconnect Technology Conference, pp. 285-287 (2002).

John Ritchie Production Group, *Production of Stents* (presentation), 15 pages (Apr. 24, 2003).

Kataoka et al., *Block Copolymer Micelles as Vehicles for Drug Delivery*, Journal of Controlled Release vol. 24, pp. 119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, vol. 37, 391-407 (1999).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kelley et al., *Totally Resorbable High-Strength Composite Material*, Advances in Biomedical Polymers, vol. 35, pp. 75-85 (1987).

Klocke et al, *How Soil Holds Water* (G90-964), http://ianrpubs.unl.edu/fieldcrops/g964.htm, printed Apr. 6, 2004, 9 pages.

Konopka, *In-Plane Moisture Transport in Nonwovens*, Nonwonvens Cooperative Research Center, NC State University, 56 pages (no date).

Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives, a companion to the Handbook of Coronary Stents*, 16 pages (1999).

Lambert et al., *Localized Arterial Wall Drug Delivery From a Polymer-Coated Removable Metallic Stent*, Circulation, vol. 90, No. 2, pp. 1003-1011 (Aug. 1994).

Lemos et al., *Coronary Restenosis After Sirolimus-Eluting Stent Implantation*, Circulation, vol. 108, No. 3, pp. 257-260 (Jul. 22, 2003).

Levy et al., *Strategies For Treating Arterial Restenosis Using Polymeric Controlled Release Implants*, Biotechnology and Bioactive Polymers, pp. 259-268 (1994).

Liermann et al., *Prophylactic Endovascular Radiotherapy Intimal Hyperplasia after Stent Implantation in Femoropopliteal Arteries*, CardioVascular and Interventional Radiology, vol. 17, pp. 12-16 (1994).

Liu et al., *Drug Release Characteristics of Unimolecular Polymeric Micelles*, Journal of Controlled Release, vol. 68, pp. 167-174 (2000).

Loeb et al., *Parylene as a Chronically Stable, Reproducible Microelectrode Insulator*, IEEE Transactions on Biomedical Engineering, pp. 121-128 (Mar. 1977).

Loh et al., *Plasma Enhanced Parylene Deposition*, Antec, pp. 1099-1103 (1991).

Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, printed Nov. 21, 2003 (2 pgs.).

Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).

Malik et al., *Overview of plasma source ion implantation research at University of Wisconsin-Madison*, J. Vac. Sci. Technol. B, No. 12, vol. 2, pp. 843-849 (Mar./Apr. 1994).

Malik et al., *Sheath dynamics and dose analysis for planar targets in plasma source ion implantation*, Plasma Sources Sci. Technol. vol. 2, pp. 81-85 (1993).

Marconi et al., *Covalent bonding of heparin to a vinyl copolymer for biomedical applications*, Biomaterials, vol. 18, No. 12, pp. 885-890 (1997).

Matsumaru et al., *Embolic Materials For Endovascular Treatment of Cerebral Lesions*, J. Biomater. Sci. Polymer Edn., vol. 8, No. 7, pp. 555-569 (1997).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull., vol. 33, No. 6, pp. 2490-2498 (1985).

Miyazawa et al., *Effects of Pemirolast and Tranilast on Intimal Thickening After Arterial Injury in the Rat*, J. Cardiovasc. Pharmacol., vol. 30, No. 2, pp. 157-162 (1997).

Moody, *Vacuum Coating Ultrasonic Transducers*, 1 page, Sensors (Dec. 1993).

Muller et al., *Advances in Coronary Angioplasty: Endovascular Stents*, Coronary Artery Disease, vol. 1, No. 4., pp. 438-448 (Jul./Aug. 1990).

Neimark et al., *Hierarchical Pore Structure and Wetting Properties of Single-Wall Carbon Nanotube Fibers*, Nano Letters, vol. 3, No. 3, pp. 419-423 (2003).

Nichols et al., *Electrical Insulation of Implantable Devices by Composite Polymer Coatings*, ISA Transactions, vol. 26, No. 4, pp. 15-18 (1987).

Nordrehaug et al., *A Novel Biocompatible Coating Applied to Coronary Stents*, EPO Heart Journal 14, p. 321 (P1694), Abstr. Suppl. (1993).

Nova Tran™ Custom Coating Services, *Parylene Conformal Coating*, 8 pages (no date).

Ohsawa et al., *Preventive Effects of an Antiallergic Drug, Pemirolast Potassium, on Restenosis After Percutaneous Transluminal Coronary Angioplasty*, American Heart Journal, vol. 136, No. 6, pp. 1081-1087 (Dec. 1998).

Olson, *Parylene, a Biostabel Coating for Medical Applications*, Specialty Coating Systems, Inc. Nova Tran™ Parylene Coating Services (no date).

Ozaki et al., *New Stent Technologies*, Progress in Cardiovascular Diseases, vol. XXXIX, No. 2, pp. 129-140 (Sep./Oct. 1996).

Para Tech Coating Company, *Galxyl, Parylene Coatings by Para Tech*, 1 page (no date).

Para Tech Coating Company, *Lab Top® Parylene Deposition System*, 2 pages (no date).

Pechar et al., *Poly(ethylene glycol) Multiblock Copolymer as a Carrier of Anti-Cancer Drug Doxorubicin*, Bioconjucate Chemistry vol. 11, No. 2, pp. 131-139 (Mar./Apr. 2000).

Peng et al., *Role of polymers in improving the results of stenting in coronary arteries*, Biomaterial, vol. 17, pp. 685-694 (1996).

Peuster et al., *A novel approach to temporary stenting: degradable cardiovascular stents produced from corrodible metal-results 6-18 months after implantation into New Zealand white rabbits*, Heart vol. 86, pp. 563-569 (2001).

Pietrzak et al., *Bioabsorbable Fixation Devices: Status for the Craniomaxillofacial Surgeon*, Journal of Craniofacial Surgery, vol. 8, No. 2, pp. 92-96 (1997).

Pietrzak et al., *Bioresorbable Implants—Practical Considerations*, Bone, vol. 19, No. 1, Supplement, pp. 109S-119S (Jul. 1996).

Poncin-Epaillard et al., *Reactivity of a Polypropylene Surface Modified in a Nitrogen Plasma*, Plasma Surface Modification of Polymers pp. 167-180 (1994).

Prabhu, *Computational Modeling in Stent-based Drug Delivery*, Business Briefing: Medical Device Manufacturing & Technology, 4 pages (2004).

Redman, *Clinical Experience with Vasovasostomy Utilizing Absorbable Intravasal Stent*, Urology, vol. XX, No. 11, pp. 59-61 (Jul. 1982).

Refracton Techonolgies, Corp., *Fine Bubble Diffusers*, 2 pages (do date).

Refracton Techonolgies, Corp., *Refractron Advanced Porous Ceramic Product Capabilities*, http://www.refractron.com/ecom/sp/cat=Product+Information, printed Apr. 6, 2004, 3 pages.

Refractron Technologies Corp., http://www.refractron.com/ecom/sp/cat=Custom+Applications, printed Jun. 24, 2003, 1 page.

Rust et al., *The Effect of Absorbable Stenting on Postoperative Stenosis of the Surgically Enlarged Maxillary Sinus Ostia in a Rabbit Animal Model*, Archives of Otolaryngology, Head and Neck Surgery, vol. 122, pp. 1395-1397 (Dec. 1996).

Sadhir et al., *The Adhesion of Glow-Discharge Polymers, Silastic And Parylene to Implantable Platinum Electrodes: Results of Tensil Pull tests After Exposure to Isotonic Sodium Chloride*, Biomaterials, vol. 2, pp. 239-243 (Oct. 1981).

Saotome, et al., *Novel Enzymatically Degradable Polymers Comprising α-Amino Acid, 1,2-Ethanediol, and Adipic Acid*, Chemistry Letters, pp. 21-24, (1991).

Schatz, *A View of Vascular Stents*, Circulation, vol. 79, No. 2, pp. 445-457 (Feb. 1989).

Scheuer et al., *Model of plasma source ion implantation in planar, cylindrical, and spherical geometries*, J. Appl. Phys., vol. 67, No. 3, pp. 1241-1245 (Feb. 1990).

Schmidt et al., *Long-term Implants of Parylene-C Coated Microelectrodes*, Medical & Biological Engineering & Computing, pp. 96-101 (Jan. 1988).

Serkova et al., *Tissue Distribution and Clinical Monitoring of the Novel Macrolide Immunosuppressant SDZ-RAD and its Metabolites in Monkey Lung Transplant Recipients: Interaction with*

Cyclosporine, The Journal of Pharmacology and Experimental Therapeutics, vol. 294, No. 1, pp. 323-332 (2000).
Serruys et al., *I Like the Candy, I Hate the Wrapper; the $^{32}$P Radioactive Stent*, Circulation, vol. 101, pp. 3-7 (Jan. 2000).
Shamim et al., *Measurement of electron emission due to energetic ion bombardment in plasma source ion implantation*, J. Appl. Phys., vol. 70, No. 9, pp. 4756-4759 (Nov. 1991).
Shamim et al., *Measurements of Spatial and Temporal Sheath Evolution for Spherical and Cylindrical Geometries in Plasma Source Ion Implantation*, J. Appl. Phys., vol. 69, No. 5, pp. 2904-2908 (Mar. 1991).
Shigeno, *Prevention of Cerebrovascular Spasm by Bosentan, Novel Endothelin Receptor*, Chemical Abstract 125:21230 (1996).
Sono Tek Corporation, *AccuMist™ for Single Stent Coating Applications*, http://www.sono-tek.com/biomedical/accumist_stent.html, printed Aug. 2, 2005, 3 pages.
Sono Tek Corporation, *MediCoat™ DES 1000, Benchtop Stent Coating System*, http://www.sono-tek.com/biomedical/medicoat_standalone.html, printed Aug. 2, 2005, 4 pages.
Sono Tek Corporation, *MicroMist for Stent Coating*, http://www.sono-tek.com/biomedical/micromist_stent.html, printed Aug. 2, 2005, 3 pages.
Spagnuolo et al., *Gas 1 is induced by VE-cadherin and vascular endothelial growth factor and inhibits endothelial cell apoptosis*, Blood, vol. 103, No. 6, pp. 3005-3012 (2004).
Specialty Coating Systems, Inc., *The Parylene Press*, 4 pages (Summer 1993).
Specialty Coating Systems, Inc., *The Parylene Press*, 6 pages (Spring 1993).
Specialty Coating Systems, Inc., *The Parylene Press*, 7 pages (Winter 1992).
Specialty Coating Systems, *Parylene and Nova Tran™ Parylene Coating Services, for Unmatched Conformal Coating Performance*, 21 pages (no date).
Specialty Coating Systems, *Parylene, a Biostable Coating for Medical Applications*, 6 pages (no date).
Specialty Coating Systems, *Repair and Recoating of Parylene Coated Printed Circuit Boards*, 15 pages (no date).
Straube, *Moisture, Materials, & Buildings*, HPAC Engineering, pp. 2-7 (no date).
Taher, *Capillary interaction between a small thin solid plate and a liquid*, Mechanical and Industrial Engineering, University of Illinois at Urbana-Champaign, 4 pages (no date).
Tamai et al., *Initial and 6-Month Results of Biodegradable Poly-I-Lactic Acid Coronary Stents in Humans*, Circulation, vol. 102, pp. 399-404 (2000).
Trident, Inc., http://www.tridentintl.com/subbody.html, printed Dec. 18, 2000, 1 page.
Trident, Inc., *Product Lines*, http://www.tridentintl.com/products-apps/ultrajet.html, printed Dec. 18, 2000, 3 pages.
Tsuji et al., *Biodegradable Polymeric Stents*, Current Interventional Cardiology Reports vol. 3, pp. 10-17 (2001).
Union Carbide Adhesion Promoters, *Union Carbide A-174 Silane*, 5 pages (Jan. 1968).
Union Carbide Electronics Devision, *Parylene Environmentally Compatible Conformal Coatings for Electronic Components Assemblies and Precision Parts*, 14 pages (no date).
Union Carbide, *Abrasion Resistance of Parylene and Other Conformal Circuit Board Coatings*, Parylene Products, No. 4, 13 pages (Oct. 1977).
Union Carbide, *Adhesion Promotion Systems for Parylene*, Parylene Products, No. 15, Revision 1, 8 pages (Oct. 1977).
Union Carbide, *Adhesion Promotion Systems for Parylene*, Technology Letter, No. 15, 13 pages (Oct. 1975).
Union Carbide, *Evaluation of Parylene and Other Pellicles as Beam Splitters*, Parylene Products, No. 8, Edited, 19 pages (Oct. 1977).
Union Carbide, *Fluorescent Parylene Coatings*, Parylene Products, No. 7 Revision 1, 8 pages (Oct. 1977).
Union Carbide, *Fluorescent Parylene Coatings*, Technology Letter, No. 7, 8 pages (Oct. 1973).
Union Carbide, *Mechanical Protection Criteria for Thin Conformal Coatings*, Parylene Products, No. 3, 21 pages (Oct. 1977).

Union Carbide, *Method for Repair and Patching of Parylene Coated Printed Circuit Boards*, Parylene Products, No. 2 Revision 1, 9 pages (Oct. 1977).
Union Carbide, *Microencapsulation by Vapor Deposition*, Parylene Products, No. 6, 12 pages (Oct. 1977).
Union Carbide, *MIL I 46058, Qualification of Parylene N, C, and D*, Parylene Products, No. 1 Revision 2, 8 pages (Oct. 1977).
Union Carbide, *Parylene Bibliography*, Parylene Products, No. 5, Revision 4, 17 pages (Jan. 18, 1982).
Union Carbide, *Parylene Conformal Coatings for Hybrid Microelectronics*, Parylene Products, No. 9, 23 pages (Oct. 1973).
Union Carbide, *Parylene Pellicles for Space Applications*, Parylene Products, No. 10, 50 pages (Oct. 1977).
Union Carbide, *Parylene Pyrolysis Kinetics*, Parylene Products, No. 11, 12 pages (Oct. 1977).
Union Carbide, *Parylene Pyrolysis Kinetics*, Technology Letter, No. 11, 12 pages (May 1974).
Union Carbide, *Parylene Removal with Oxygen Plasmas*, Parylene Products, No. 18, 7 pages (Aug. 1977).
Union Carbide, *Printed Circuit Board Masking Techniques for Use with Parylene*, No. 14, Revision 1, 11 pages (Oct. 1977).
Union Carbide, *Solvent Resistance of the Parylenes*, Parylene Products, No. 12, Revision 1, 5 pages (Oct. 1977).
Union Carbide, *The Selective Removal of Parylene by Plasma Etching*, No. 13, Revision 1, 7 pages (Oct. 1977).
Union Carbide, *Thermal Endurance of the Parylenes in Air*, Parylene Products, No. 16, 4 pages (Mar. 1976).
Union Carbide, *Vapor Phase Adhesion Promotion Systems*, Parylene Products, No. 17, Revision 1, 11 pages (Oct. 1977).
van Beusekom et al., *Coronary Stent Coatings*, Coronary Artery Disease, vol. 5, No. 7, pp. 590-596 (Jul. 1994).
van der Giessen et al., "Edge Effect" of $^{32}$P *Radioactive Stents is Caused by the Combination of Chronic Stent Injury and Radioactive Dose Falloff*, Circulation, vol. 104, pp. 2236-2241 (Oct. 30, 2001).
Vapor Inc., *Vapore-Jet™ Capillary Pump—How it Works*, http://www.vapore.com/tech_howto.htm, printed Aug. 13, 2003, 2 pages.
Völkel et al., *Targeting of immunoliposomes to endothelial cells using a single -chain Fv fragment directed against human endoglin (CD105)*, Biochemica et Biophysica Acta, vol. 1663, pp. 158-166 (Apr. 15, 2004).
von Recum et al., *Degradation of polydispersed poly(L-lactic acid) to modulate lactic acid release*, Biomaterials, vol. 16, pp. 441-445 (1995).
Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).
Wilensky et al., *Methods and Devices for Local Drug Delivery in Coronary and Peripheral Arteries*, Trends Cardiovasc. Med., vol. 3, No. 5, pp. 163-170 (1993).
Wong et al., *An Update on Coronary Stents*, Cardio, 8 pages (Feb. 1992).
World Precision Instruments, Inc., http://www.wpiinc.com/WPI_Web/Pumps/pneumatic_Fig.gif, printed Sep. 30, 2002, 1 page.
World Precision Instruments, Inc., *Nanoliter Injector*, http://www.wpiinc.com/WPI_Web/Microinjection/Nanoliter_Injector.html, printed Jun. 10, 2005, 3 pages.
World Precision Instruments, Inc., *Nanoliter Injector*, http://www.wpi-europe.com/products/microinjection/nanoliter.htm printed Jun. 10, 2005, 2 pages.
World Precision Instruments, Inc., *Pneumatic PicoPumps*, http://www.wpieurope.com/products/microinjection/picopumps.htm, printed Jun. 10, 2005, 4 pages.
World Precision Instruments, Inc., *Pneumatic PicoPumps*, http://www.wpiinc.com/WPI_Web/Microinjection/Pneumatic_PicoPumps.html, printed Jun. 10, 2005, 4 pages.
Yau et al., *Modern Size-Exclusion Liquid Chromatography*, Wiley-Interscience Publication, 9 pages (1979).
Yokoyama et al., *Characterization of physical entrapment and chemical conjugation of adriamycin in polymeric micelles and their design for in vivo delivery to asolid tumor*, Journal of Controlled Release, vol. 50, pp. 79-92 (1998).

Yuen et al., *Tissue response to potential neuroprosthetic materials implanted subdurally*, Biomaterials, vol. 8, pp. 57-62 (Mar. 1987).

Zhmud et al., *Dynamics of Capillary Rise*, Journal of Colloid in Interface Science, vol. 228, pp. 263-269 (2000).

Zimarino et al., *Analysis of Stent Edge Restenosis with Different Forms of Brachytherapy*, The American Journal of Cardiology, vol. 89, pp. 322-325 (Feb. 1, 2002).

Zylberman et al., *Comparative Study of Electroless Co(W,P) an Co(Mo,P) Thin-Films for Capping and Barrier Layers for Cu Metallization*, 2002 Advanced Metallization Conference, 2 pages (no date).

* cited by examiner

![Air inlet] ![Liquid inlet]

Insulating nozzle
120

110

Primary atomization zone

Ring electrode
130

High voltage
140

Resistance

Field line

Stent strut

APPARATUS AND METHOD FOR ELECTROSTATIC COATING OF AN ABLUMINAL STENT SURFACE

TECHNICAL FIELD

This invention relates to apparatus and method for electrostatic coating of stents, more specifically to a stent mandrel fixture used during the electrostatic coating process.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend can be applied to the stent by immersing the stent in the composition or by spraying the composition onto the stent. The solvent is allowed to evaporate, leaving on the surfaces a coating of the polymer and the therapeutic substance impregnated in the polymer.

The dipping or spraying of the composition onto the stent can result in a complete coverage of all stent surfaces, i.e., both luminal (inner) and abluminal (outer) surfaces, with a coating. However, from a therapeutic standpoint, drugs need only be released from the abluminal stent surface, and possibly the sidewalls. Moreover, having a coating on the luminal surface of the stent can have a detrimental impact on the stent's deliverability as well as the coating's mechanical integrity. A polymeric coating can increase the coefficient of friction between the stent and the delivery balloon. Additionally, some polymers have a "sticky" or "tacky" nature. If the polymeric material either increases the coefficient of friction or adherers to the catheter balloon, the effective release of the stent from the balloon upon deflation can be compromised. Severe coating damage at the luminal side of the stent may occur post-deployment, which can result in a thrombogenic surface. Accordingly, there is a need to eliminate or minimize the amount of coating that is applied to the inner surface of the stent. Reducing or eliminating the polymer from the stent luminal surface also means a reduction in total polymer load, which will minimize the material-vessel interaction and is therefore a desirable goal for optimizing long-term biocompatibility of the device.

A method for preventing the composition from being applied to the inner surface of the stent is by placing the stent over a mandrel that fittingly mates within the inner diameter of the stent. A tubing can be inserted within the stent such that the outer surface of the tubing is in contact with the inner surface of the stent. With the use of such mandrels, some incidental composition can seep into the gaps or spaces between the surfaces of the mandrel and the stent, especially if the coating composition includes high surface tension (or low wettability) solvents. Moreover, a tubular mandrel that makes contact with the inner surface of the stent can cause coating defects. A high degree of surface contact between the stent and the supporting apparatus can provide regions in which the liquid composition can flow, wick, and/or collect as the composition is applied to the stent. As the solvent evaporates, the excess composition hardens to form excess coating at and around the contact points between the stent and the support apparatus, which may prevent removal of the stent from the supporting apparatus. Further, upon removal of the coated stent from the support apparatus, the excess coating may stick to the apparatus, thereby removing some of the coating from the stent and leaving bare areas. In some situations, the excess coating may stick to the stent, thereby leaving excess coating composition as clumps or pools on the struts or webbing between the struts. Accordingly, there is a tradeoff when the inner surface of the stent is masked in that coating defects such as webbing, pools and/or clumps can be formed on the stent.

In addition to the above mentioned drawbacks, other disadvantages associated with dip and spray coating methods include lack of uniformity of the produced coating as well as product waste. The intricate geometry of the stent presents a great degree of challenges for applying a coating material on a stent. Dip coating application tends to provide uneven coatings and droplet agglomeration caused by spray atomization process can produce uneven thickness profiles. Moreover, a very low percentage of the coating solution that is sprayed to coat the stent is actually deposited on the surfaces of the device. A majority of the sprayed solution is wasted in both application methods.

To achieve better coating uniformity and less waste, electrostatic coating deposition has been proposed. Examples in patent literature covering electrostatic deposition include U.S. Pat. Nos. 5,824,049 and 6,096,070. Briefly, referring to FIG. 1, for electro-deposition or electrostatic spraying, a stent 100 is grounded and gas is used to atomize the coating solution into droplets 110 as the coating solution is discharged out from a nozzle 120. The droplets 110 are then electrically charged by passing through an electrical field created by a ring electrode 130 which is in electrical communication with a voltage source 140. The charged particles are attracted to the grounded metallic stent. An alternative design for coating a stent with an electrically charged solution is disclosed by U.S. Pat. No. 6,669,980. U.S. Pat. No. 6,669,980 teaches a chamber that that contains a coating formulation that is connected to a nozzle apparatus. The coating formulation in the chamber is electrically charged. Droplets of electrically charged coating formulation are created and dispensed through the nozzle and are deposited on the grounded stent. Stents coated with electrostatic technique have many advantages over dipping and spraying methodology, including, but not limited to, improved transfer efficiency (reduction of drug and/or polymer waste), high drug recovery on the stent due to elimination of re-bounce of the coating solution off of the stent, and better coating uniformity, and a faster coating process. Formation of a coating layer on the inner surface of the stent is not, however, eliminated with the used of electrostatic deposition. With the use of mandrels that ground the stent and provide for a tight fit between the stent and the mandrel, formation of coating defects such as webbing, pooling and clumping remain a problem. If a space is provided between the mandrel and the stent, such that there is only minimal contact to ground the stent, the spraying can still penetrated into the gaps between the stent struts and coat the inner surface of the stent. Conventional stent geometry does not provide for a good Faraday cage due to the interspace between the struts of the stent. As illustrated by FIG. 2, electric field lines can penetrated into the opening between the struts and deposit a coating on the inner surface of the stent. This is known as the "wrap around" effect. Charged particles are not only disposed on the outer surface of the stent, but also are wrapped around each strut and are attracted to the inner surface of the stent.

Accordingly, what is needed is an apparatus and method that allows for electro-deposition or electrostatic spraying of a stent while eliminating or minimizing the wrap around effect.

SUMMARY

In accordance with one embodiment of the invention a stent mandrel fixture to support a stent during application of a charged coating substance to the stent is provided, comprising a first mandrel component in conductive contact with the stent and a second mandrel component positioned at least partially within a bore of the stent, the second mandrel component being made from a nonconductive material, being coated with a nonconductive material or having a nonconductive sleeve disposed thereon. The first mandrel component can provide for a charge differential to the stent relative to the coating substance. The nonconductive material or the sleeve is capable of collecting a charge of the same polarity as the coating substance. In some embodiments, the coating substance includes a conductive solvent.

In accordance with another embodiment, a fixture to support a stent during application of a charged coating substance to the stent is provided, comprising a mandrel component extending at least partially through a longitudinal bore of the stent, the mandrel component being configured to minimize or eliminate the wrap around effect of the charged coating substance around the stent struts to prevent or reduce the amount of coating substance applied to an inner side of the stent. The mandrel component includes an element configured to collect charged particles applied to the component. The mandrel component includes an element configured to repel charged particles applied to the component. The fixture can also include a second mandrel component in electrical communication with the stent. The second mandrel component is for applying a charge to the stent and/or to ground the stent.

In accordance with another embodiment, an electrostatic spray coating apparatus for electrostatic application of a substance to a stent is provided comprising a stent mandrel fixture having a first mandrel component in conductive contact with the stent, a second mandrel component positioned at least partially within a bore of the stent, the second mandrel component configured to repel charged particles so as to eliminate any, or reduce the amount of, coating substance applied to an inner side of the stent, a coating substance dispenser positioned at a distance away from the stent, and a power source to charge the coating substance.

In accordance with other embodiments, methods of coating a stent with a substance are provided. The method can include supporting a stent on a mandrel, charging the coating substance, applying the coating substance to the stent, and applying a charge to the stent and/or grounding the stent via the first mandrel component. In one embodiment, the method comprising applying charged particles to a part of the mandrel prior the applying the coating substance to the stent.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 1 is a block diagram illustrating an electrostatic spray coating system;

FIG. 2 illustrates the wrap around effect on a stent strut;

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

It is believed that the embodiments of the invention can provide for a uniform coating, prevent excess waste associated with conventional dip and spray coating processes, and prevent a coating from being formed on the inner surface of the stent or reduce the amount of coating that is formed on the inner surface of the stent. This reduces the total polymer load on a stent, thereby improving long-term biocompatibility and ensuring that most of the coating is on the abluminal surface where it provides the most benefit. Further, problematic interactions between a delivery mechanism (e.g., delivery balloon) and the stent luminal surface are eradicated, thereby increasing the ease of stent deliverability.

Figure 3:
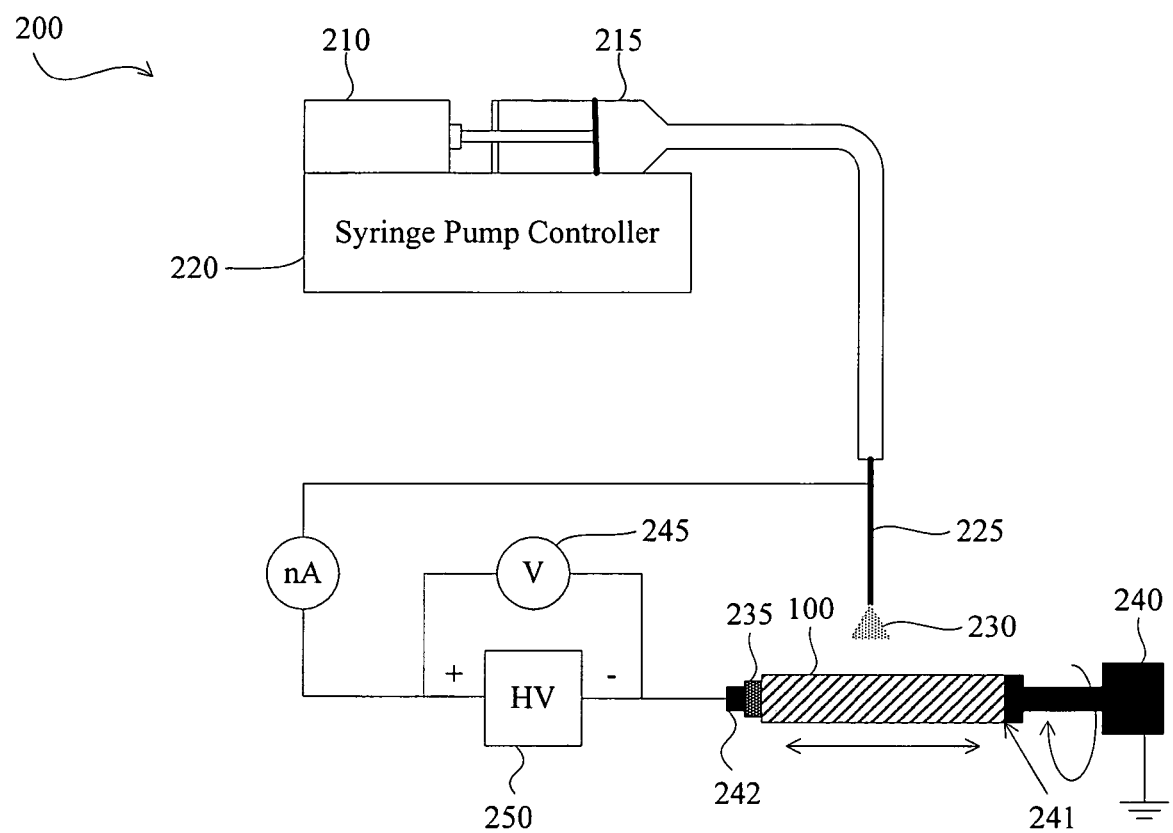
FIG. 3 is a block diagram illustrating an electrostatic spray coating system.

FIG. 3 illustrates an electrostatic spray coating system 200. The system 200 includes a syringe pump controller 220 communicatively coupled to a pump 210 (e.g., a Harvard syringe pump model 11) that pumps a syringe 215 holding a composition. As discussed further below, the composition can include any type of a coating material such as solvent(s), polymer(s), therapeutic substance(s) or any one or combination of these. The syringe 215 dispenses the composition onto the stent 100 via a metallic dispensing tip, hypotube 225 or other dispenser that is coupled to the syringe 215.

Figure 4A:
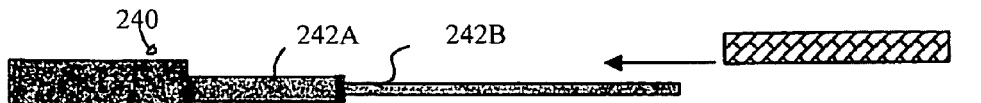
FIGS. 4A, 4B and 4C illustrate a mandrel in accordance with one embodiment of the invention.
Figure 4B:
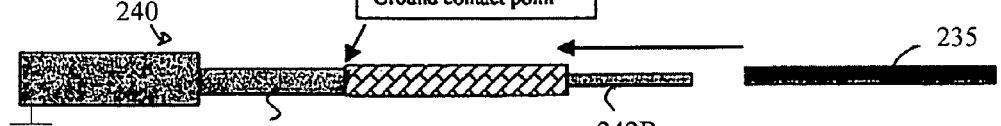
Figure 4C:
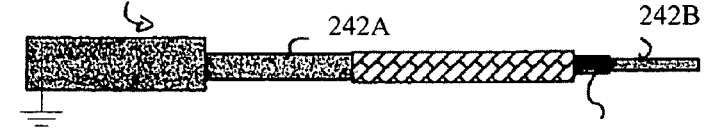

The stent 100 is mounted on a stent mandrel fixture 240 that can provide translational and rotational movement of the stent 100 during a coating process. The stent 100 can be located, for example, approximately 20-25 mm downstream from the hypotube 225. As illustrated by FIGS. 4A, 4B and 4C, the mandrel fixture 240 includes a mandrel arm 242 that can extend partially or all the way through the bore of the stent 100. The mandrel arm 242 includes a larger first diameter section 242A extending to a smaller second diameter section 242B. The larger diameter section 242A should be of sufficient size to allow one end of the stent 100 to be crimped thereon or to allow for a friction fit within the one end of the stent 100. The fitting should be tight enough that the stent 100 is supported over the smaller diameter section 242B without making contact with section 242B. In other words, a gap is disposed between the outer surface of the smaller diameter section 242B and the inner surface of the stent 100. The larger diameter section 242B should be made from a conductive material, such as a metal, so as to allow for charge transmission from the stent 100. In one embodiment, the smaller diameter section 242 can be made from a non-conductive material such as a rubber, plastic, polymer or ceramic material. Alternative, the smaller diameter section 242B can also be made of a conductive material or other material and insulated with a sleeve 235 made from a non-conductive material (also referred to interchangeably as an insulating material) such as rubber, plastic, polymer or ceramic material. Particular examples include pellethane, nylon, Teflon, polyvinylchloride (PVC), etc. Non-conductive, insulator or insulating refers to the ability of a material to prevent the flow of electric current between or among points. Insulation resistance can be measured in megaohms per stated volume or area. In some embodiments, insulator, insulating or non-conductive means less or significantly less conductive that the segment of the mandrel fixture 240 that grounds and/or applies a charge to the stent, so long as the insulating or non-conductive component(s) of the fixture 240 reduces or prevents the wrap around effect for eliminating or minimizing the formation of the coating on the inner surface of a stent.

In yet another embodiment, smaller diameter section 242B can be coated with an insulating material. As used herein, insulating sleeve and coating, although very different in form, will be used interchangeably for brevity. The same concepts that are disclosed with the sleeve apply equally with the use of a coating. With the use of the sleeve 235, the smaller diameter section 242B must of sufficiently small diameter so as to allow for the gap to exist between the sleeve 235 and the inner surface of the stent 100. The insulating sleeve 235 can have a length equal to at least about the length of the stent 100. Shorter length sleeves can be used to provide for the wrap around effect at an end of the stent. This may be suitable if it is desired to provide for more drug at one end of the stent. The sleeve 235 can be in tubular form. The sleeve 235 can also be patterned so as to provide some areas where the conductive mandrel 240 is exposed so as to selectively be able to coat designated areas of the inner surface of the stent 100. This may be desirable in order to provide some degree of friction or adhesiveness between a balloon and the stent. In one embodiment of the invention, the sleeve 235 has an inner diameter of about 0.042 inches and an outer diameter of about 0.054 inches. The thickness of the sleeve 235 depends on the material used. The gap or spacing between the luminal surface of the stent 100 and the outer diameter of the sleeve 235 (or the outer surface of a nonconductive smaller diameter section 252B or a coating) can be about 0.005 inches, for example.

Figure 5A:
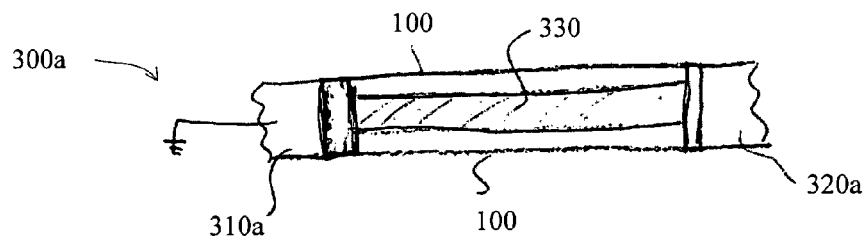
FIGS. 5A, 5B and 5C illustrate the mandrel in accordance with various other embodiments of the invention.

Referring to FIG. 5A, in accordance with another embodiment, a mandrel fixture 300a can include a support member 310a that engages or is disposed in one end of the stent 100 and a lock member 320a that engages or is disposed in the opposing end of the stent 100. The support member 310a and the lock member 320a can be coupled together by a mandrel arm 330 that extends through the longitudinal bore of the stent 100. The arm 330 can be permanently coupled to the support member 310a and releasable coupled to the lock member 320a, such as by a screw fit or a friction fit. The support member 310a and/or lock member 320a can be in conductive communication with the stent 100. In one embodiment, the mandrel arm 330 can be made from a non-conductive material or alternatively the sleeve 235 can be disposed over the arm 330. Again, a coating can be used in lieu of the sleeve 235. In some embodiments, one of the support member 310a and the lock member 320a can also be made from a non-conductive material, have an insulating sleeve disposed thereon or be coating with an insulating material.

Figure 5B:
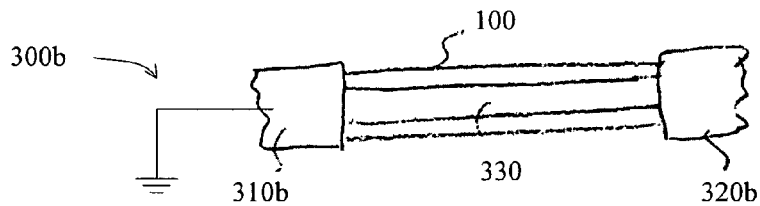

With the use of the mandrel fixtures of FIGS. 4A, 4B, 4C, it is possible that some coating defects can be formed in the areas of the end ring segment or segments of the stent 100 that are disposed over that the mandrel section 242A. The coating composition can be equally attracted to the mandrel and form areas of coating conglomeration between the stent struts that are positioned over section 242A. This would be equally true for the embodiment of FIG. 5A as there are now overlapping areas at both ends of the stent 100. To minimize coating defects, the stent 100 can be locked between two surfaces as illustrated in the mandrel fixture 300b of FIG. 5B. The support member 310b and the lock member 320b of FIG. 5B provide ends that are larger than the diameter of the stent 100—as positioned on the fixture—so as to allow the stent 100 to be pinched there between. In some embodiments, the stent 100 can be threaded over the arm 330 and placed against the support member 310b. The lock member 320b is then screwed or friction fitted onto the arm 330 and moved incrementally closer to the support member 310b so as to gently pinch the stent 100 there between. A certain degree of manual adjustment may be necessary to center the stent 100. The support member 310b and/or the lock member 320b can be made from a conductive material so as to ground the stent 100. If only one of the members 310b or 320b is in electrical communication with the stent 100, the other member as well as the arm 300 can be made from a non-conductive material or can be insulated with a sleeve or a coating.

Figure 5C:
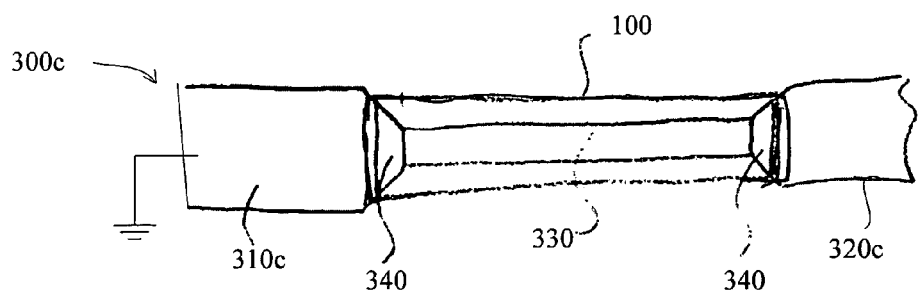

In another embodiment of the invention, a mandrel fixture 300c, as shown in FIG. 5C, includes a support member 310c and/or a lock member 320c that can have a coning end portion 340 that penetrates partially into the stent 100 ends and allows the stent 100 to rest thereon. With this embodiment, the necessity of manually centering the stent 100 is eliminated. In one embodiment, at least one of the coning end sections 340 can be made from a conductive material. The other end 340 as well as the arm 330 can be made from a non-conductive material, or can be insulated with a sleeve or a coating. In some embodiments, a segment of a tip of the conductive coning end or ends 340 that is disposed within the stent 100 can be made from a nonconductive material or can be insulated by a sleeve or a coating. In some embodiments, the tip 340 should be large enough so as to allow for nominal conductive contact between the fixture 300c and the stent 100. The wrap around effect, therefore is further reduced at the stent 100 ends.

In some embodiments, the non-conductive or insulated segment of the mandrel fixture 240 should expand across and beyond the length of the stent or a majority of the length of the stent 100 so as to eliminate or minimize any coating from being formed on the inner surface of the stent 100. However, as discussed above, the coverage of the non-conductive or insulating segment of the mandrel fixture 240 can be adjusted so as to allow for some coating to be formed on the inner surface of the stent 100. In some embodiments the total length of the inner surface that is protected from the wrap around effect can be greater than 99%, 95%, 90%, 80%, 70%, 60% or 50%.

Referring back to FIG. 3, a power source 245 is coupled to a high voltage transformer 250 that converts voltage from the power source 245 to a high voltage (e.g., up to 20 kV), which is then applied to the hypotube 225. The high voltage ionizes the composition into atomized ionized (e.g., negatively or positively charged) droplets in a spray 230 without the need for atomizing air. However, in an embodiment of the invention, the hypotube 225 may be replaced by an air-assisted atomization nozzle, which connects to an atomizing air source to provide atomizing air to assist in atomization of the composition. The atomization can be external or internal.

Atomization of the composition using electrospray is governed by the Rayleigh Limit, which holds that droplets can be broken apart if the charge of the droplets exceeds the surface tension of the droplets. Specifically, the maximum charge of a droplet is related to the surface tension as follows:

$$Q=8\pi\sqrt{\epsilon_o\gamma R^3}$$

wherein $\epsilon_o$ is the permittivity of a vacuum or medium in which the droplets are atomized; γ is the surface tension of the liquid the droplet is made of; and R is radius of the droplet. Accordingly, a sufficiently high voltage must be applied to the composition to impart a high enough charge to overcome the surface tension.

The stent 100 is in electrical contact with the stent mandrel fixture 240 at point 241 (for FIG. 4, at an end of the §tent 100) such that any charge applied to the stent 100 is conducted to the mandrel 240. The stent mandrel fixture 240 may be grounded and/or electrically connected to a power source 245 via one end of the mandrel 242, as will be discussed further below, to form a complete circuit. Therefore, the stent 100 does not collect charge having the same polarity as the atomized ionized droplets of the spray 230. The insulating sleeve 235 (or the coating or the non-conductive segment of the mandrel fixture 240) is an insulator and therefore does not conduct charge. Any charge dispensed onto the sleeve 235 (e.g., from the spray 230) will therefore build up and not be transmitted.

During a coating process, the hypotube 225 dispenses the composition as an ionized and atomized spray 230 onto the stent 100, which is rotated and translated to ensure that the abluminal surface of the stent 100 is fully and uniformly coated. Charge from the ionized spray 230 does not build up on the stent 100. In an embodiment of the invention, the stent mandrel fixture 240 can be coupled to the power source 245, which will therefore pull any charge from the stent 100 thereby leaving the stent 100 neutrally charged or having a charge opposite of the ionized spray 230 (e.g., having a positive charge). If a charge having the same polarity as the ionized spray 230 were to build up on the stent 100, the stent 100 would repel the ionized spray 230, thereby preventing coating of any surface of the stent 100. In contrast, the insulating sleeve 235 does build a charge having the same polarity as the ionized spray 230. Accordingly, the insulating sleeve 235 will repel the atomized ionized spray 230 from the interior diameter of the stent 100. The wrap around effect is therefore reduced or eliminated.

The components of the coating substance or composition can include a solvent or a solvent system comprising multiple solvents; a polymer or a combination of polymers; and/or a therapeutic substance or a drug or a combination of drugs. Representative examples of polymers that can be used to coat a stent or medical device include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether esters) (e.g. PEO/PLA); polyalkylene oxalates; polyphosphazenes; biomolecules, such as fibrin, fibrinogen, cellulose, starch, collagen and hyaluronic acid; polyurethanes; silicones, polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof. Solvents should have a high enough conductivity to enable ionization of the composition if the polymer or therapeutic substance is not conductive. For example, acetone and ethanol have sufficient conductivities of $8\times10^{-6}$ and ~$10^{-5}$ siemen/m, respectively.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

Figure 6:
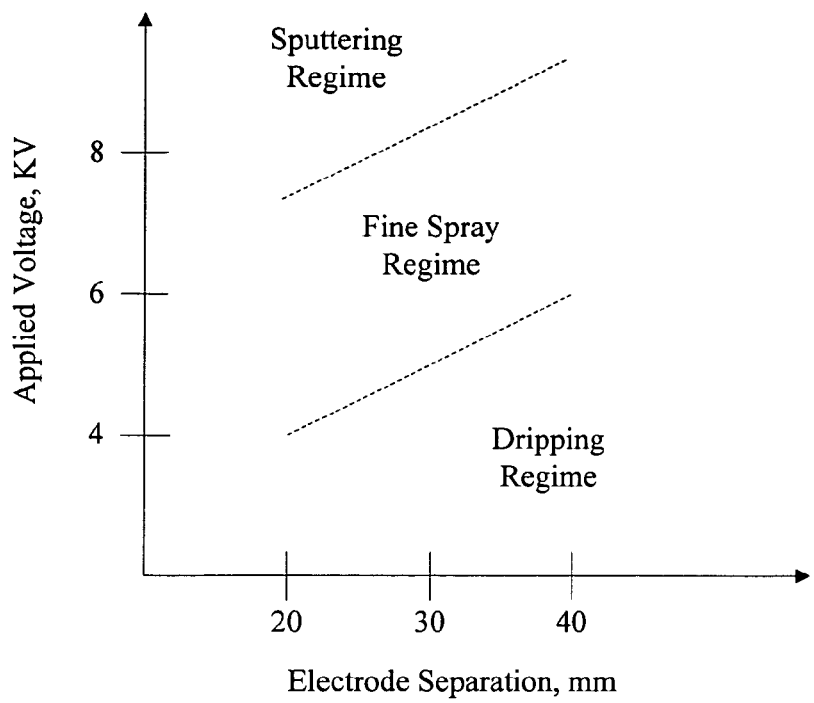
FIG. 6 is chart illustrating spray regimes as a function of applied voltage and electrode separation.
Figure 7:
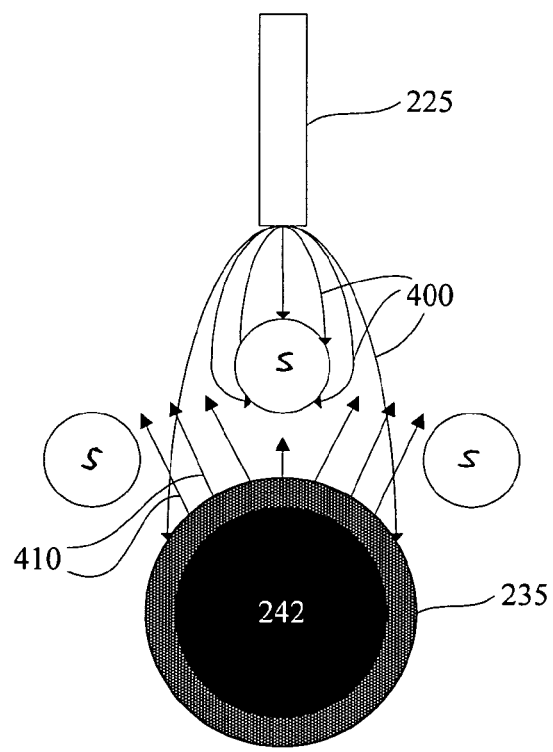
FIG. 7 is a magnified cross section of a stent strut with no wrap around effect.
Figure 8:
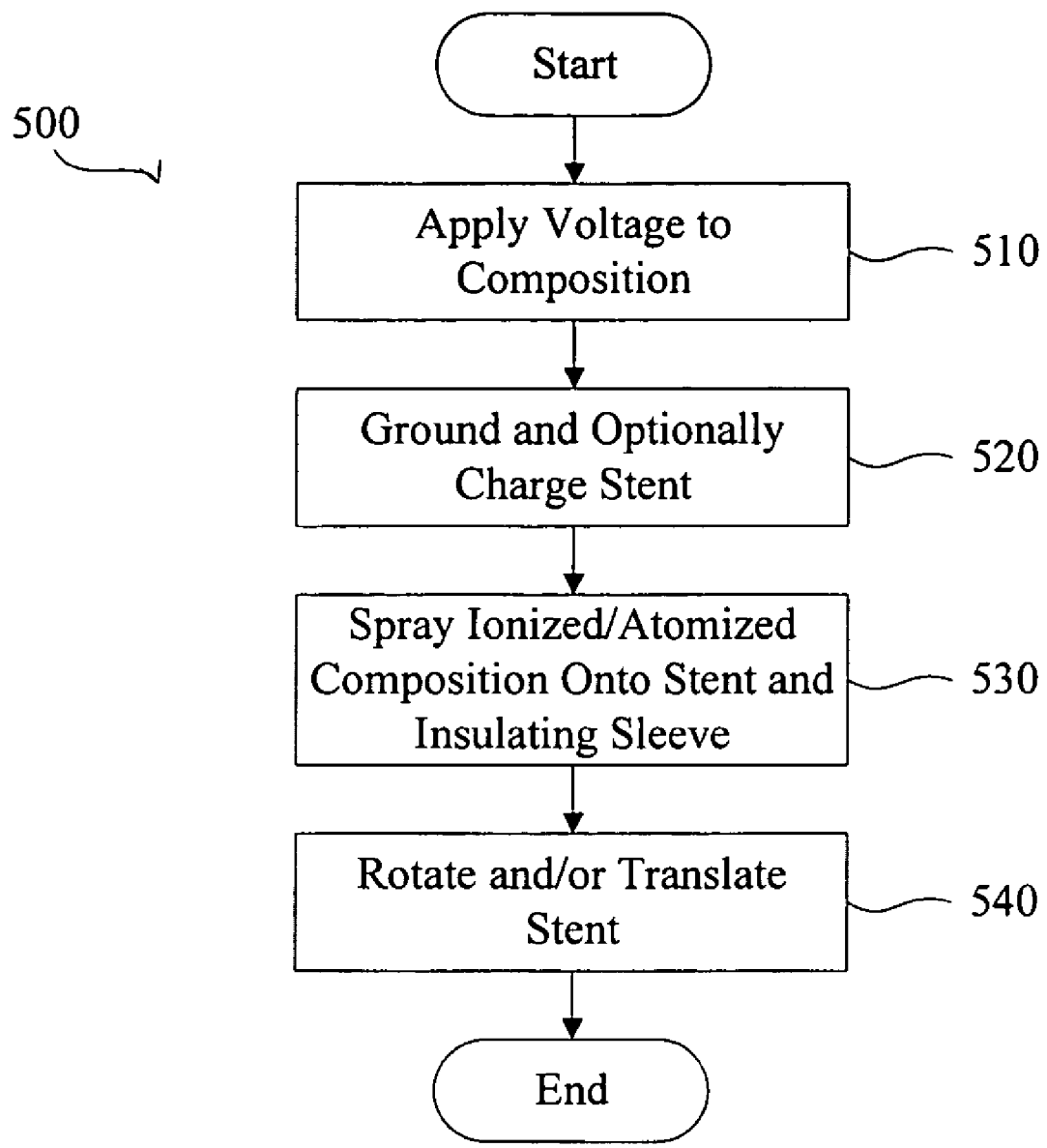
FIG. 8 is a flowchart illustrating a method of electrostatic spray coating.

FIG. 6 is chart illustrating spray regimes as a function of applied voltage and electrode separation. Applied voltage is based on the power source 245 and the high voltage transformer 250. Electrode separation refers to the distance between the stent 100 and the hypotube 225. Ideally, appropriate voltage is applied to the hypotube 225 to enter the fine spray regime, which provides adequate atomization. If inadequate voltage is applied to the hypotube 225, there will not be sufficient atomization, thereby causing the composition to exit the hypotube 225 as a drip instead of as the atomized spray 230. Too much voltage on the other hand will lead to a sputtering regime in which the composition exits the hypotube 225 in spurts instead of as the atomized spray 230.

FIG. 7 is a diagram illustrating a magnified cross section of a portion of the electrostatic spray coating system 200. Electric field lines 400 extend downward from the hypotube 225 towards struts S of the stent 100. In addition, the electric field lines 400 wrap around the struts S and can extend towards the insulating sleeve 235. During a spray coating process, initially, the spray 230 follows the electric field lines 400 coating the insulating sleeve 235, the abluminal surface of the stent 100, and slightly coating the luminal surface of the stent 100.

During the initial stages of the spray coating process, a charge of the same polarity as the spray 230 builds up on the insulating sleeve 235, thereby generating electric field lines 410 that counteract the electric field lines 400. The electric field lines 410 extend outward from the insulating sleeve 235 and prevent and repel the spray 230 from further coating the luminal surface of the stent 100. Accordingly, coating of the luminal surface of the stent 100 is substantially limited. In an embodiment of the invention, the insulating sleeve 235 (or coating or nonconductive mandrel parts) can come pre-charged so that the electric field lines 410 are generated prior to the beginning of the spray coating process, thereby preventing or reducing any coating of the luminal surface of the stent 100 with the spray 230. The insulating sleeve 235 (or coating or nonconductive mandrel parts) can be pre-charged by, for example, spraying the sleeve 235 or coating before loading the stent 100 onto the system 200.

In some embodiments, during the spray coating process, the stent 100 is in electrical contact with the stent mandrel fixture 240 and is grounded and can be supplied with a charge opposite the charge of the spray 230. The fixture 240 can be supplied with an opposite charge by electrically coupling the fixture 240 to the power source 245, which supplies a first charge to the spray 230 and an opposite charge to the fixture 240. This difference in polarity increases the attraction of the spray 230 to the stent 100, therefore increasing coating of the stent 100. This difference in polarity can also compensate for misalignment of the hypotube 225 with the stent 100, which is a critical issue during the conventional applications of a composition to a drug releasing stent. Specifically, the polarity difference will pull the spray 230 towards the stent 100 even if the stent 100 is not positioned directly beneath the hypotube 225.

FIG. 5 is a flowchart illustrating a method 500 of electrostatic spray coating. In an embodiment of the invention, the system 200 executes the method 500. First, a high voltage is applied (510) to the composition as it travels through the hypotube 225, which ionizes and atomizes the composition so that it can be ejected as atomized ionized spray 230. The stent 100 is then grounded and optionally charged (520) so that there is a charge or polarity differential between the spray 230 and the stent 100 so that the stent 100 attracts the spray 230. The ionized atomized composition is then sprayed (530) onto the stent 100 and the insulating sleeve 235, thereby forming a charge on the sleeve 235 so that any additional spray 230 is repelled from the sleeve 235 and therefore the luminal surface of the stent 100. In an alternative embodiment, the sleeve 235 may be pre-charged (e.g., by spraying the sleeve 235 before loading the stent 100 onto the mandrel fixture) and so the spraying (530) only covers the abluminal surface of the stent 100. The stent 100 is also rotated and translated (540) during the spraying (530) so that the entire abluminal surface of the stent 100 can be coated. The method 500 then ends.

It will be appreciated by one of ordinary skill in the art that the applying (510), grounding/charging (520), spraying (530), and rotating/translating (540) can occur in any order and is not limited to the order disclosed above. Further, the applying (510), grounding/charging (520), spraying (530), and rotating/translating (540) can occur substantially simultaneously instead of sequentially.

The following examples are provided:

EXAMPLE 1

In an example spray process, parameters according to Table I were used. The composition comprised 2% weight Poly(DL-Lactide) in 80/20 acetone/cyclohexanone solvent mixture. A blue dye was added to the formulation to replace the drug and to provide the contrast. The polymer to dye ratio was 1 to 1. The stent mandrel fixture was grounded through a wire with an alligator clip. The spray cycle was programmed for 10-seconds spray and 10-seconds drying cycle. The total coating weight was 630 μg. The stent was an 18 mm Vision stent available from Guidant. A pellethane tube was used between the stent and the mandrel to create the repulsive force.

TABLE I

| | |
|---|---|
| Mandrel Spin Rate | 150 RPM |
| Start Position | 25 mm |

TABLE I-continued

| | |
|---|---|
| End Position | 54 mm |
| Dry Position | 120 mm |
| Drying Nozzle Temperature Set Point | 60° C. |
| Drying Air Pressure | 23 PSI |
| Electrode Separation | 20-25 mm |
| Applied Voltage | 4-10 KV |

EXAMPLE 2

Cleaned 18 mm Vision stents (Guidant Corp.) were first primered with 2 wt % of poly(butyl methacrylate) solution using a modified N1537 spray coater and the coating weight was in the range of 75 to 90 μg. The primered stents were mounted on a metallic mandrel with one additional metallic collet, which was used to support the stent and to provide the contact points for ground. The mandrel was grounded through a wire with an alligator clip. SOLEF formulation was used for the drug coat of everolimus (190 μg dose with polymer to drug ration of 3.12 to 1). SOLEF is a trade name of poly(vinylidene fluoride-co-hexafluoropropene) available from Solvay Fluoropolymers, Inc. of Houston, Tex. The deposited rate per spray cycle was controlled in the range of 15 to 20 μg. The spray cycle was programmed for 10-seconds spray and 10-seconds dry cycle. The drying temperature was set at 60 deg. C. and the air pressure was set at 23 psi. A post oven bake at 50 deg. C. for 1 hour was conducted and the coating weight on the 18 mm Vision stents were targeted in the range of 785 μg to 835 μg.

EXAMPLE 3

A bare metal stent was mounted over a metallic spray mandrel. The mandrel was grounded through a wire with an alligator clip. D, L-PLA formulation, 80/20 acetone to cyclohexanone with 1:1 polymer to everolimus ratio, was used for the drug coating. The deposit rate per spray cycle was controlled in the range of 70 to 80 μg. The voltage was controlled between 6 to 8 KV. The spray cycle was programmed for 10-seconds spray and 10-seconds dry cycle. The dry temperature was set at 60 deg. C. and the air pressure was set at 23 psi. A post bake at 50 deg. C. for 1 hour was conducted and the coating weight on the 18 mm stent was targeted in range of 630 μg to 730 μg.

While particular embodiments of the present invention have been shown and described, it will be obvious to one of ordinary skill in the art that changes and modifications can be made without departing from this invention in its broader aspects. For example, after application of the coating to the abluminal surface of the stent 100 as described above, the luminal surface of the stent 100 can be coated with a different coating via spray coating, electroplating or other technique. Therefore, the appended claims are to encompass within their scope all such changes and modifications as fall within the true spirit and scope of this invention.

What is claimed is:

1. A stent mandrel fixture to support a stent during application of a charged coating substance to the stent, comprising:
    a first mandrel component in conductive contact with the stent, the first mandrel component including a support element to contact one end of the stent and a lock element to contact the other end of the stent; and
    a second mandrel component connecting the support element to the lock element and positioned at least partially within a bore of the stent, the second mandrel component being spaced from the walls of the bore, having an outermost surface exposed to the walls of the bore, and being made from a nonconductive material or being coated with a nonconductive material.

2. The fixture of claim 1, wherein the first mandrel component provides a charge differential to the stent relative to the coating substance.

3. The fixture of claim 1, wherein the first mandrel component is electrically coupled to a power source to provide a charge to the stent having a polarity opposite of the coating substance.

4. The fixture of claim 1, wherein the nonconductive material or the sleeve is capable of collecting a charge of the same polarity as the coating substance.

5. The fixture of claim 1, wherein the coating substance includes a conductive solvent.

6. The fixture of claim 1, wherein the support element or the lock element is made from a non-conductive material, is coated with a non-conductive material or has a non-conductive sleeve disposed thereon.

7. The fixture of claim 1, wherein the support element includes a coning end portion that penetrates into an end of the stent.

8. The fixture of claim 7, wherein a tip of the coning end portion is made from a non-conductive material, is coated with a non-conductive material or has a non-conductive sleeve disposed thereon.

9. The fixture of claim 1, wherein the lock element includes a coning end portion that penetrates into an end of the stent.

10. The fixture of claim 9, wherein a tip of the coning end portion is made from a non-conductive material, is coated with a non-conductive material or has a non-conductive sleeve disposed thereon.

11. The fixture of claim 1, wherein the first mandrel component is in contact with an end segment of the stent.

12. The fixture of claim 1, wherein the second mandrel component has an outer surface and the outer surface does not abut a surface of the bore.

13. A fixture to support a stent during application of a charged substance to the stent, comprising: a mandrel arm including a first section having a first diameter, the first section being in conductive contact with an end of the stent; and a second section having a second diameter, less than the first diameter, disposed coaxially with the first section, extending at least partially through a longitudinal bore of the stent and spaced from the walls of the bore, the second section being configured to receive the charged substance on its outermost surface so as to minimize or eliminate the wrap around effect of the charged substance around stent struts to prevent any substance from being applied to an inner side of the stent or to reduce the amount of substance applied to an inner side of the stent.

14. The fixture of claim 13, wherein the second section includes an element configured to collect charged particles applied to the element.

15. The fixture of claim 13, wherein the second section includes an element configured to repel charged particles applied to the element.

16. The fixture of claim 15, wherein the element is the charged substance.

17. The fixture of claim 13, wherein the first section is for applying a charge to the stent and/or to ground the stent.

18. The fixture of claim 13, wherein the mandrel arm is configured for supporting the stent as a cantilever.

* * * * *